US012703681B2

(12) United States Patent
Pathi et al.

(10) Patent No.: US 12,703,681 B2
(45) Date of Patent: Aug. 11, 2026

(54) METHODS FOR THE PREPARATION OF SPHINGOSINE 1-PHOSPHATE RECEPTOR MODULATORS AND SOLID FORME THEREOF

(71) Applicant: CIPLA LIMITED, Mumbai (IN)

(72) Inventors: Srinivas Laxminarayan Pathi, Bangalore (IN); Puppala Ravi Kumar, Bangalore (IN); Ramanaiah Chennuru, Nellore (IN); Durga Surya Narayana Yarra, Bangalore (IN); Yellanki Jagannadham, Bangalore (IN); Siva Krishna Nangedda, Mandavalli (IN); Lakkireddy Pullareddy, Kumbhagiri Village (IN); Raju Barla, Peddapalli (IN)

(73) Assignee: CIPLA LIMITED, Mumbai (IN)

( * ) Notice: Subject to any disclaimer, the term of this patent is extended or adjusted under 35 U.S.C. 154(b) by 867 days.

(21) Appl. No.: 18/000,121

(22) PCT Filed: May 27, 2021

(86) PCT No.: PCT/IN2021/050515
§ 371 (c)(1),
(2) Date: Nov. 28, 2022

(87) PCT Pub. No.: WO2021/240547
PCT Pub. Date: Dec. 2, 2021

(65) Prior Publication Data

US 2023/0212115 A1 Jul. 6, 2023

(30) Foreign Application Priority Data

May 29, 2020 (IN) ............................ 202021022647
Sep. 9, 2020 (IN) ............................ 202021038947
Nov. 17, 2020 (IN) ............................ 202021050037

(51) Int. Cl.
*C07D 205/04* (2006.01)
*C07C 49/76* (2006.01)
*C07C 55/14* (2006.01)
*C07C 207/00* (2006.01)

(52) U.S. Cl.
CPC ............ *C07D 205/04* (2013.01); *C07C 49/76* (2013.01); *C07C 55/14* (2013.01); *C07C 207/00* (2013.01); *C07B 2200/13* (2013.01)

(58) Field of Classification Search
CPC .... C07D 205/04; C07C 49/76; C07B 2200/13
See application file for complete search history.

(56) References Cited

U.S. PATENT DOCUMENTS 7,939,519 B2 5/2011 Pan
9,604,914 B2 3/2017 Gallou
11,673,860 B2 * 6/2023 Martinelli ............ C07D 205/04 548/953
2018/0118678 A1 5/2018 Ciszewski

FOREIGN PATENT DOCUMENTS

WO 2004/103306 A2 12/2004
WO 2010/080409 A1 7/2010
WO 2019/064184 A1 4/2019
WO 2019/144094 A1 7/2019

OTHER PUBLICATIONS

Mino R Caira et al., "Crystalline Polymorphism of Organic Compounds", Topics in Current Chemistry; Springer, Berlin, DE, vol. 198, Jan. 1, 1998 (Jan. 1, 1998) pp. 163-208.
International Search Report & Written Opinion for PCT/IN2021/050515, mailed on Dec. 7, 2021.

* cited by examiner

*Primary Examiner* — Kamal A Saeed
(74) *Attorney, Agent, or Firm* — Kramer & Amado, P.C.

(57) ABSTRACT

The present invention relates to process for preparation of 1-(4-{1-[(E)-4-cyclohexyl-3-trifluoromethyl-benzyloxy imino]ethyl}-2-ethyl-benzyl)-azetidine-3-carboxylic acid, intermediates, salts and solid forms thereof to pharmaceutical compositions comprising the salts and solid forms and to use of said compositions for the treatment of multiple sclerosis, particularly secondary progressive multiple sclerosis.

14 Claims, 11 Drawing Sheets

METHODS FOR THE PREPARATION OF SPHINGOSINE 1-PHOSPHATE RECEPTOR MODULATORS AND SOLID FORME THEREOF

FIELD OF THE INVENTION

This invention relates to novel processes for synthesizing 1-(4-{1-[(E)-4-cyclohexyl-3-trifluoromethyl-benzyloxy imino]ethyl}-2-ethyl-benzyl)-azetidine-3-carboxylic acid, to intermediates and solid forms thereof that are used in such processes and pharmaceutical compositions thereof.

BACKGROUND OF THE INVENTION

Multiple sclerosis (MS) is a chronic disorder of the CNS that affects around 2.3 million people worldwide. There are three main forms of MS: RRMS (the most common form of the condition at diagnosis), PPMS (primary progressive MS) and SPMS (secondary progressive multiple sclerosis). MS disrupts the normal functioning of the brain, optic nerves and spinal cord through inflammation and tissue loss.

SPMS follows an initial form of RRMS, which accounts for approximately 85% of all MS diagnoses, and is characterized by gradual worsening of neurological function over time. This leads to a progressive accumulation of neurological disability. There remains a high unmet need for safe and effective treatments to help delay disability progression in SPMS with active disease (with relapses and/or evidence of new MRI activity).

Siponimod is a selective sphingosine-1-phosphate receptor modulator for oral use that is used for the treatment of adults with relapsing forms of multiple sclerosis, including secondary progressive multiple sclerosis (SPMS) with active disease, relapsing remitting multiple sclerosis (RRMS) and clinically isolated syndrome (CIS). It is intended for once-daily oral administration.

Siponimod, is chemically termed as 1-(4-{1-[(E)-4-cyclohexyl-3-trifluoromethyl-benzyloxy imino]ethyl}-2-ethyl-benzyl)-azetidine-3-carboxylic acid (hereinafter referred to as Compound I), Compound I

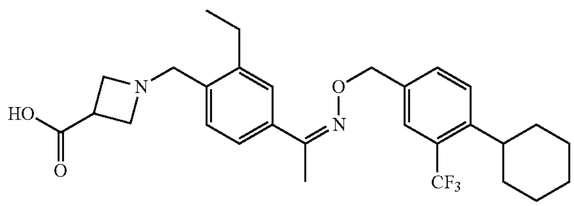 [SMILES: CCc1cc(/C(C)=N\OCc2ccc(C3CCCCC3)c(C(F)(F)F)c2)ccc1CN1CC(C(=O)O)C1]

Siponimod and its salt was first known from the following patents applications: U.S. Pat. No. 7,939,519 B2 (US '519)/WO2004/103306/US 2018/0118678 A1. These patent applications disclose the compound, a process for its manufacture, a specific salt form of this compound and the use of the compound or its salt in a pharmaceutical composition to treat multiple sclerosis via inhibition of the proliferation of target cells, alone or in combination with further therapeutic agents.

The process described in US '519 is schematically represented below:

Scheme 1

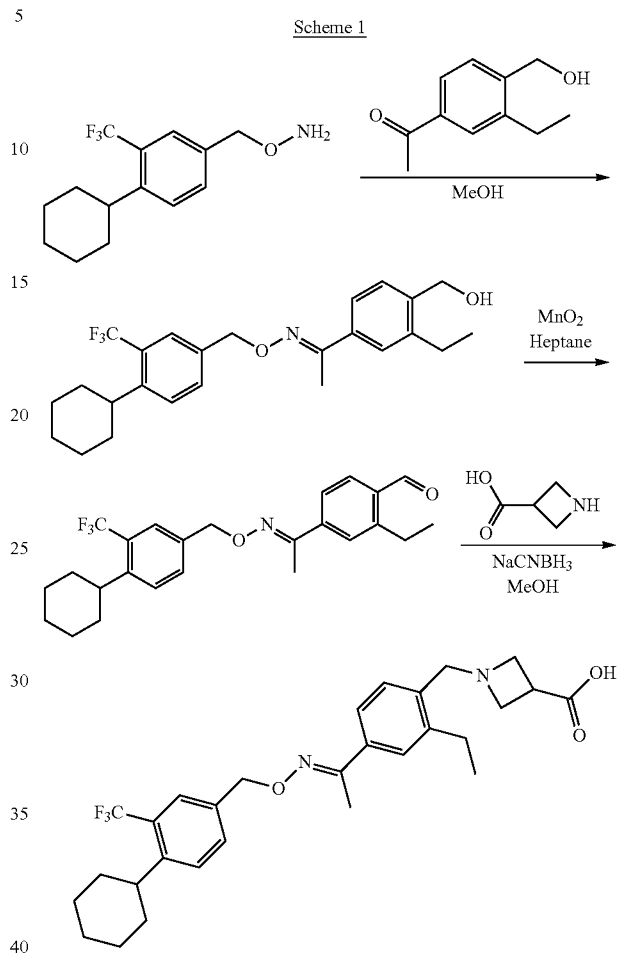

U.S. Pat. No. 9,604,914 B2 disclose alternate process to prepare Siponimod and its monofumarate salt. The process is schematically represented below:

Scheme 2

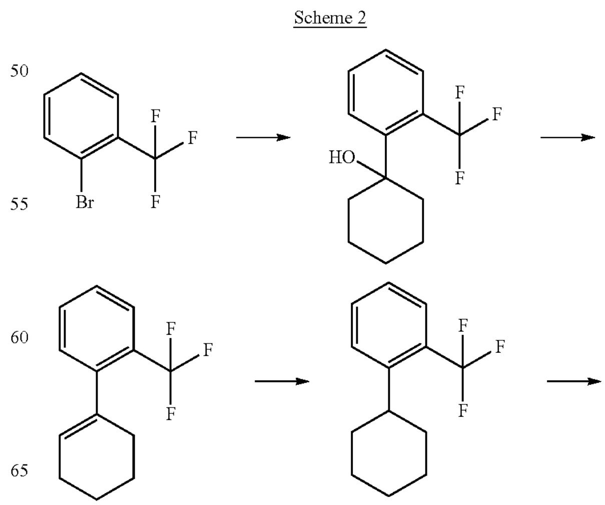

-continued
-continued
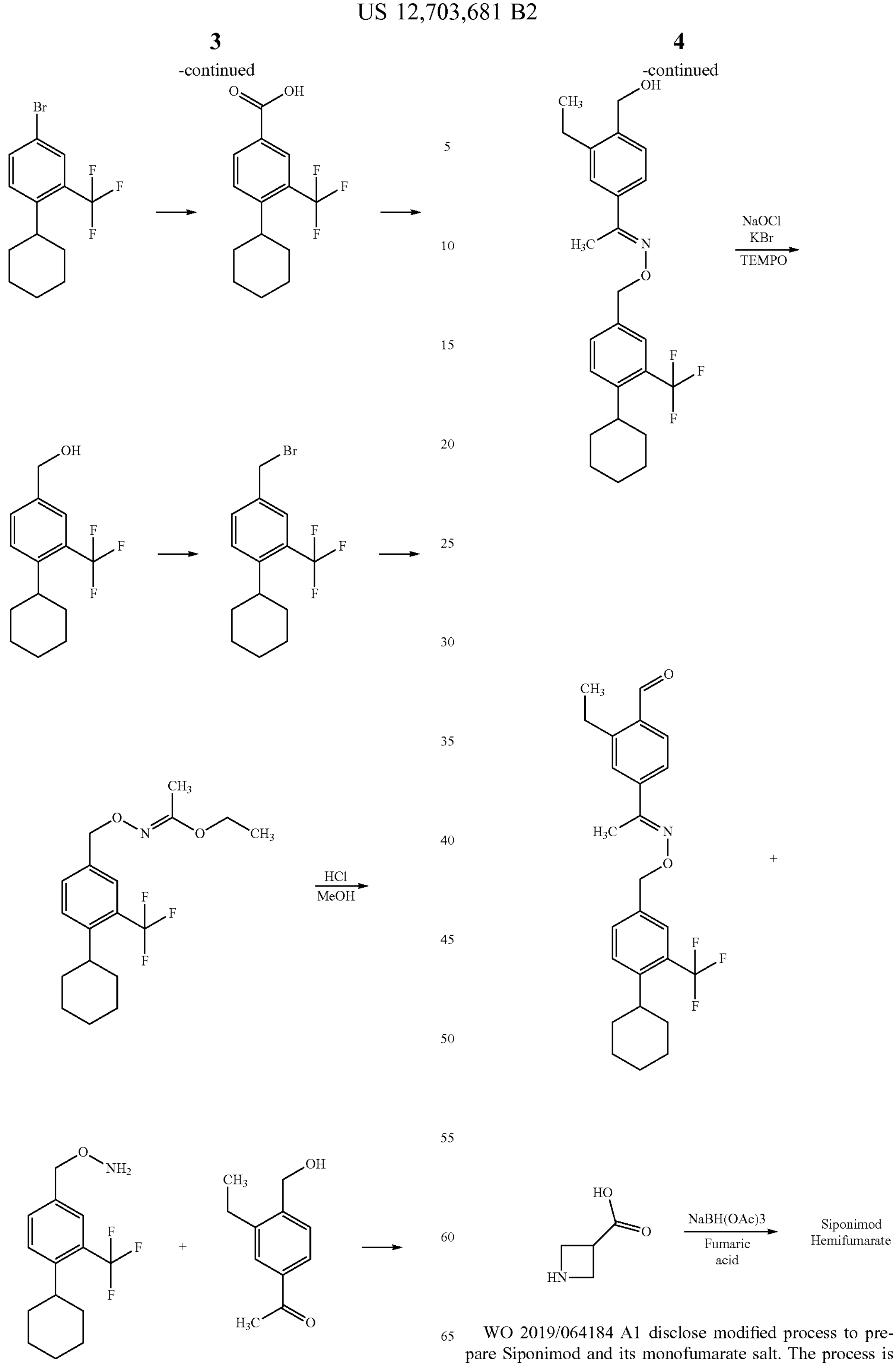
WO 2019/064184 A1 disclose modified process to prepare Siponimod and its monofumarate salt. The process is schematically represented below:

Scheme 3
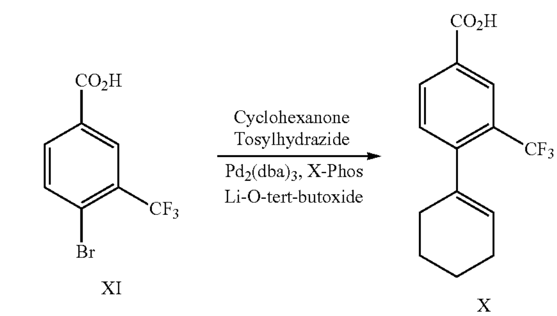
XI X
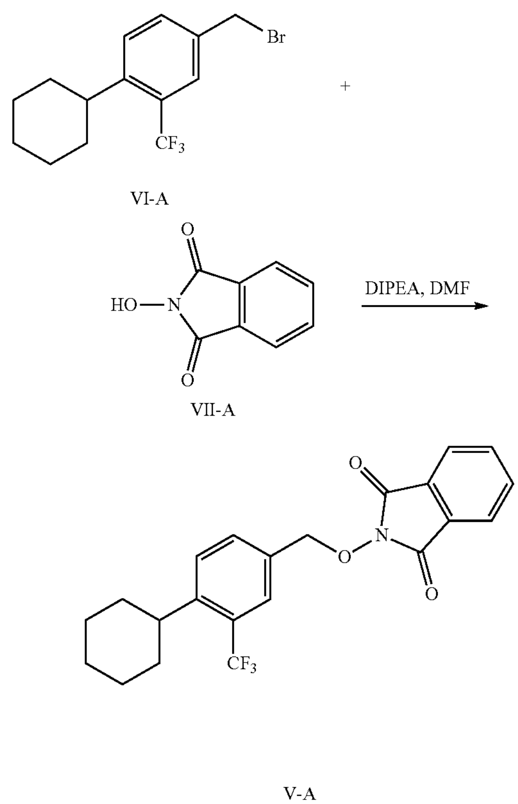
VI-A
VII-A
V-A
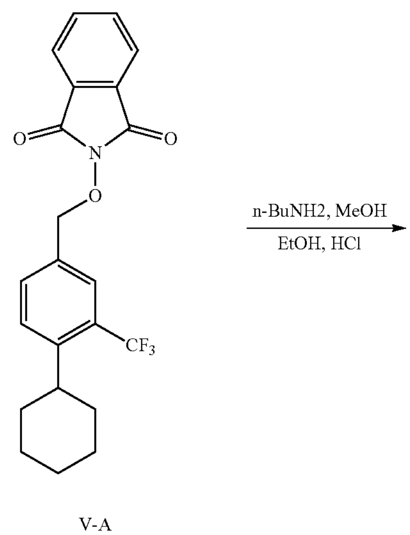
V-A
-continued
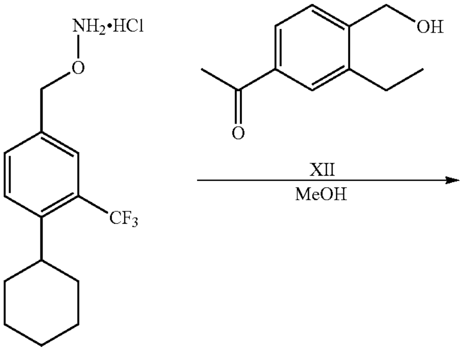
IV
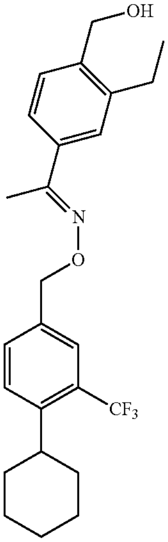
III
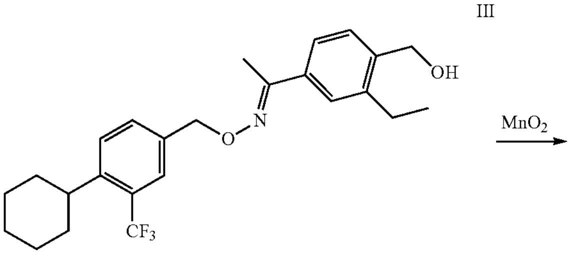
III
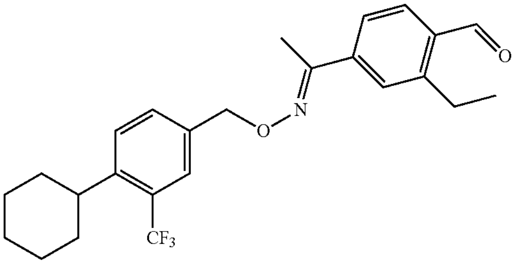
II -continued

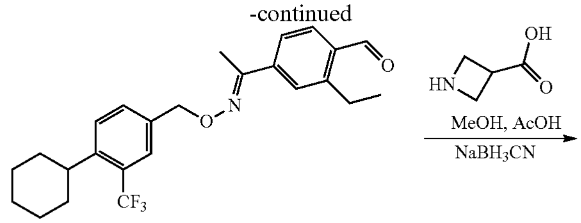

II

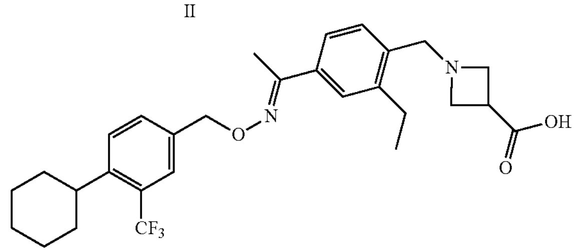

I

Although the above-mentioned patent applications already describe a process to manufacture the Siponimod and its salts, thereof an object of the present invention is a new improved and commercially viable process for the manufacture of this compound.

Further, crystalline forms and/or salts of Siponimod can possess advantageous properties in terms of their solubility and/or stability and/or bioavailability and/or impurity profile and/or filtration characteristics and/or drying characteristics and/or their ability to be handled and/or micronized and/or preparation of solid oral forms.

It has now been found that the aqueous solubility of Siponimod, especially the solubility in a gastric or intestinal environment may be distinctly enhanced by combining this drug with certain organic acids.

In view of the foregoing, it would also be desirable to provide new forms of Siponimod. Additionally, the various forms of Siponimod could be used to prepare improved pharmaceutical compositions

OBJECT OF THE INVENTION

The object of the present invention is to provide processes for the preparation of Siponimod or pharmaceutically acceptable salts thereof.

Another object of the present invention is to provide novel intermediates that are useful in the synthesis of Siponimod or pharmaceutically acceptable salts thereof.

Yet another object of the present invention is to provide a process which is simple, economical and suitable for industrial scale-up.

Yet another object of the present invention is to provide novel solid state forms of Siponimod such as novel crystalline forms and co-crystals.

Yet another object of the present invention is to provide a process for the preparation of novel solid state forms of Siponimod.

Yet another object of the invention is to provide pharmaceutical composition comprising a therapeutically effective amount of novel solid state forms of Siponimod and at least one pharmaceutically acceptable carrier Yet another object of the invention is to provide method of treatment of human or animal body by therapy, wherein novel solid state forms of Siponimod, are useful.

SUMMARY OF THE INVENTION

This invention is directed to methods of preparing Siponimod of Formula I or pharmaceutically acceptable salts of Siponimod and intermediates thereof and to the solid state forms thereof.

In a first embodiment, the invention provides a process for preparing Siponimod of Formula I

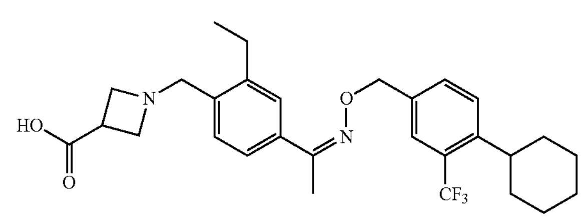

which comprises: converting compound of Formula IV

IV

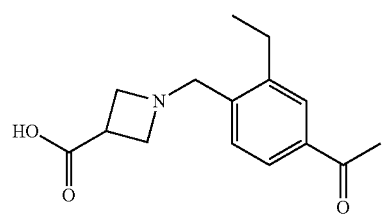

to Siponimod of Formula I

In one embodiment conversion comprises, a) reacting compound of Formula IV with hydroxyl amine to provide compound of Formula III

III

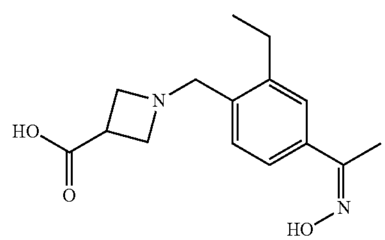

and;

b) condensing compound of Formula III with compound of Formula II

II

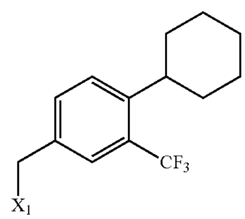

wherein $X_1$ is a leaving group selected from bromo, chloro, iodo and fluoro;

in the presence of a suitable base to provide Siponimod of Formula I.

In an alternative embodiment, conversion comprises, reacting compound of Formula IV with compound of Formula VIII

VIII

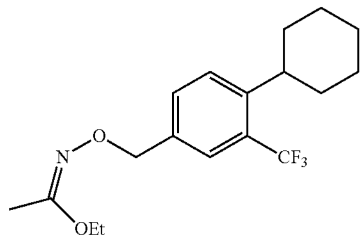

to provide Siponimod of Formula I.

In a second embodiment, the invention provides a compound of Formula IV

IV

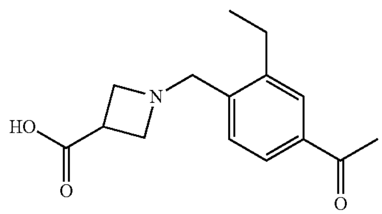

In a third embodiment, the invention provides a process for preparing compound of Formula IV, which comprises:

reacting compound of Formula VI

VI

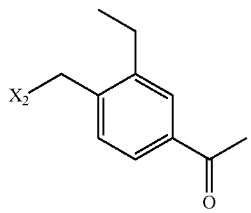

wherein $X_2$ is a leaving group selected from halo such as chloro, bromo and iodo; mesylate, tosylate, trilate, brosylate or phosphonate;

with compound of Formula V

V

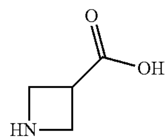

in the presence of a suitable base, to provide a compound of Formula IV

In a fifth embodiment, the invention provides a compound of Formula VI

VI

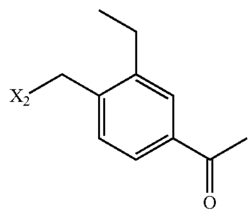

wherein $X_2$ is a leaving group selected from halo such as chloro, bromo and iodo; mesylate, tosylate, trilate, brosylate or phosphonate.

In a sixth embodiment, the invention provides a process for preparing compound of Formula VI, which comprises reacting compound of Formula VII

VII

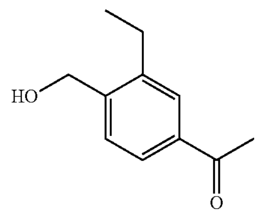

with a suitable leaving group, preferably halogenating agent to provide a compound of Formula VI.

In a seventh embodiment, the invention provides a compound of Formula III

III

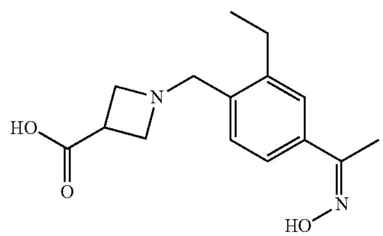

In an eighth embodiment, the invention provides a process for preparing compound of Formula III, which comprises reacting compound of Formula IV with hydroxyl amine to provide compound of Formula III.

In a ninth embodiment, the invention provides yet an alternate process for preparing Siponimod of Formula I

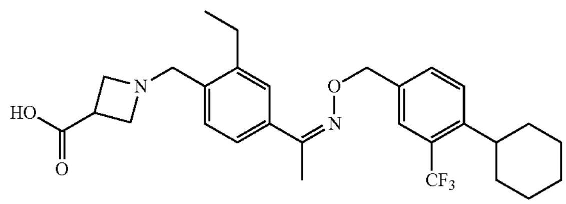 [SMILES: CCc1cc(/C(C)=N\OCc2ccc(C3CCCCC3)c(C(F)(F)F)c2)ccc1CN1CC(C(=O)O)C1]

which comprises: converting compound of Formula XI

XI

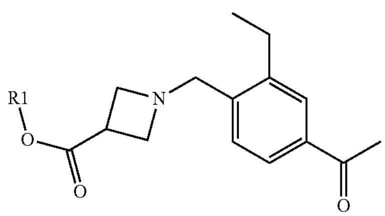

wherein R1 is C1-C4 alkyl, selected from methyl, ethyl, n-propyl, isopropyl, n-butyl and t-butyl; to Siponimod of Formula I In an embodiment conversion comprises, a) reacting compound of Formula XI with compound of Formula IX or a salt thereof.

IX

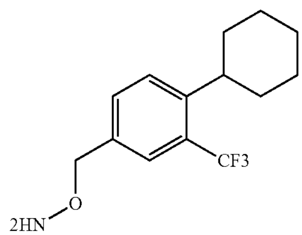

to provide compound of Formula X or salt

X

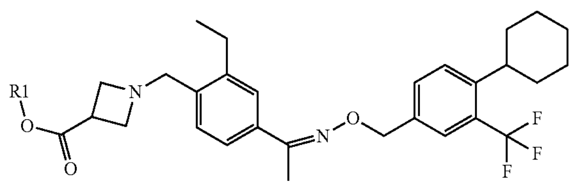

wherein R1 is as defined above, and;

b) hydrolyzing compound of Formula X or salt in the presence of a suitable acid or base to provide Siponimod of Formula (I).

In a tenth embodiment, the invention provides a compound of Formula XI

XI

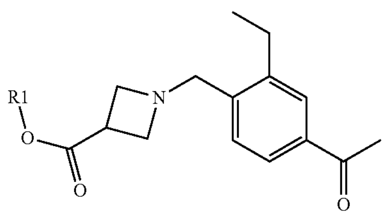

wherein R1 is C1-C4 alkyl, selected from methyl, ethyl, n-propyl, isopropyl, n-butyl and t-butyl.

In an eleventh embodiment, the invention provides a process for preparing compound of Formula XI.

In one embodiment the process comprises:

reacting compound of Formula XIII

XIII

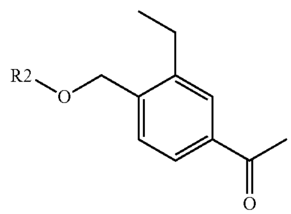

wherein R2 is suitable leaving group selected from alkyl sulfonyl, aryl sulfonyl, acetyl, with compound of Formula XII

XII

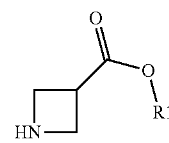

wherein R1 is C1-C4 alkyl, selected from methyl, ethyl, n-propyl, isopropyl, n-butyl to provide compound of Formula XI.

In an alternative embodiment the process comprises:

reacting compound of Formula VI

VI

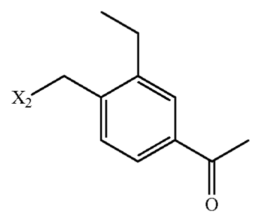

wherein $X_2$ is a suitable leaving group; with compound of Formula XII

XII

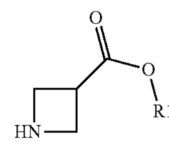

in the presence of a suitable base, to provide a compound of Formula XI

In a twelfth embodiment, the invention provides a compound of Formula XIII

XIII

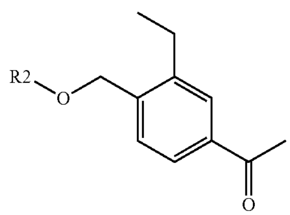

wherein R2 is suitable leaving group selected from alkyl sulfonyl, aryl sulfonyl, acetyl.

In a thirteenth embodiment, the invention provides a process for preparing compound of Formula XIII, which comprises: reacting compound of Formula VII,

VII

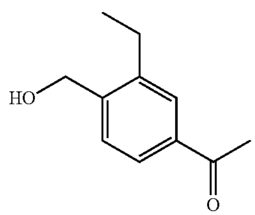

with suitable protecting group to provide a compound of Formula XIII.

In a fourteenth embodiment, the invention provides a process for preparing compound of Formula IX or salt thereof,

IX

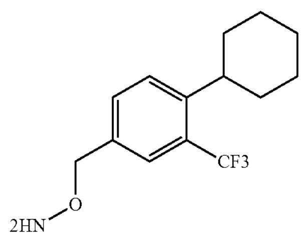

the process comprises:

reacting compound of Formula II

II

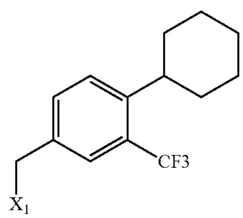

wherein $X_1$ is a leaving group selected from bromo, chloro, iodo and fluoro; with n-hydroxy phthalimide of Formula XV

XV

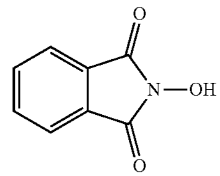

in the presence of a suitable base and suitable solvent to provide compound of Formula XIV

XIV

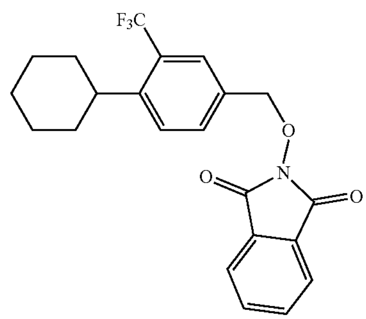

and;

reacting compound of Formula XIV with hydrazine or salt thereof in the presence of suitable solvent to provide compound of Formula IX and optionally converting to salt.

In a fifteenth embodiment, the invention provides novel compounds III, IV, VI, IX XI and XIII. The compounds may be prepared according to the processes described above.

In a sixteenth embodiment, the invention provides Siponimod or its pharmaceutically acceptable salt thereof prepared by a process as described above.

In a seventeenth embodiment, the invention provides crystalline Siponimod fumarate Form-C1.

In an eighteenth embodiment, the invention provides a process for the preparation of crystalline Siponimod fumarate Form-C1.

In a nineteenth embodiment, the invention provides crystalline Siponimod fumarate Form-C2.

In a twentieth embodiment, the invention provides a process for the preparation of crystalline Siponimod fumarate Form-C2.

In a twenty first embodiment, the invention provides a co-crystal of Siponimod and adipic acid, pharmaceutical compositions containing the co-crystal, and methods of administering the co-crystal to a patient for treating a disease.

In a twenty second embodiment, the invention provides co-crystal of Siponimod and glutaric acid, pharmaceutical compositions containing the co-crystal, and methods of administering the co-crystal to a patient for treating a disease.

In a twenty third embodiment, the invention provides crystalline Siponimod fumarate Form-C3.

In a twenty fourth embodiment, the invention provides a process for the preparation of crystalline Siponimod fumarate Form-C3.

In a twenty fifth embodiment, the invention provides a pharmaceutical composition comprising Siponimod or its pharmaceutically acceptable salt or crystalline polymorphs or co-crystal thereof, prepared by a process as described above, together with one or more pharmaceutically acceptable excipients. Such excipients are well known to those skilled in the art.

In a twenty sixth embodiment, the invention provides the use of Siponimod or its pharmaceutically acceptable salt or crystalline polymorphs or co-crystal thereof, prepared by a process as described above in medicine.

In a twenty seventh embodiment, the invention provides Siponimod or its pharmaceutically acceptable salt or crystalline polymorphs or co-crystal thereof, prepared by a process as described above for use in the treatment of adults with relapsing forms of multiple sclerosis.

In a twenty eighth embodiment, the invention provides the use of Siponimod or its pharmaceutically acceptable salt or crystalline polymorphs or co-crystal thereof, prepared by a process as described above, in the manufacture of a medicament for treating adults with relapsing forms of multiple sclerosis.

In a twenty ninth embodiment, the invention provides the use of Siponimod or its pharmaceutically acceptable salt or crystalline polymorphs or co-crystal thereof, prepared by a process as described above in the treatment of adults with relapsing forms of multiple sclerosis.

In a thirtieth embodiment, the invention provides a method of treating relapsing forms of multiple sclerosis in a patient in need of such treatment, which method comprises administering to the patient a therapeutically effective amount of Siponimod or its pharmaceutically acceptable salt or crystalline polymorphs or co-crystal thereof, prepared by a process as described above.

DETAILED DESCRIPTION OF THE EMBODIMENTS

Figure 1:
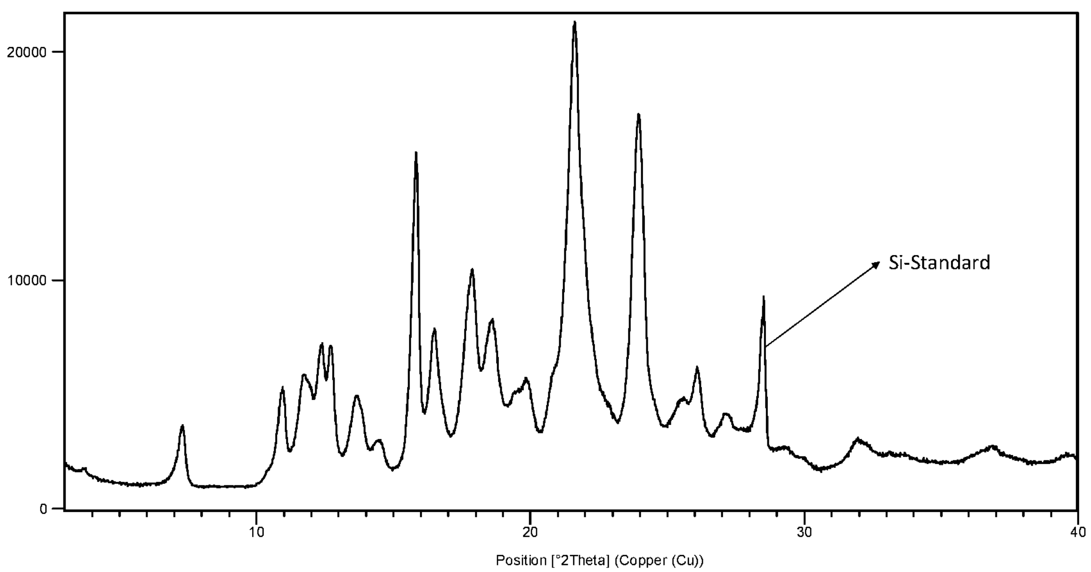
FIG. 1 depicts X-Ray Powder Diffraction (XRPD) pattern of crystalline Siponimod fumarate Form-C1

The present invention provides a process for the preparation of Siponimod which process is economical, fast and which results in a high purity Siponimod product.

In an embodiment, Siponimod or a pharmaceutically acceptable salt thereof, is prepared by a process which comprises converting compound of Formula IV to Siponimod of Formula I.

Accordingly, one embodiment of the process for the preparation of Siponimod is as shown in Scheme 4.

Scheme 4

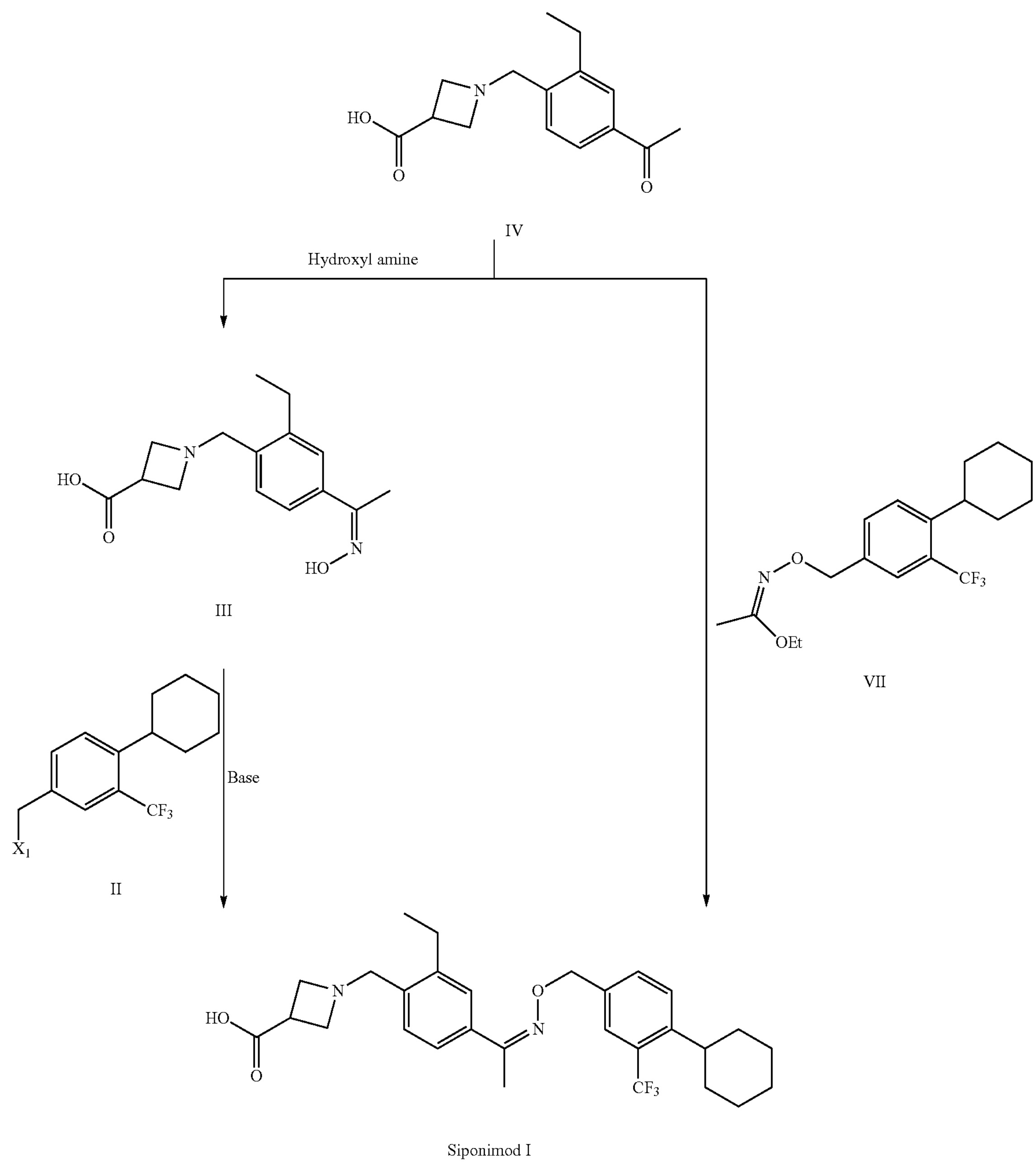

wherein $X_1$ is a leaving group selected from bromo, chloro, iodo and fluoro, preferably bromo or chloro.

The compound of Formula III and IV are hitherto unreported intermediates useful in the process for the preparation of Siponimod as described herein.

In an embodiment ketone of Formula IV is reacted with hydroxylamine salt in the presence of a suitable base to provide ketoxime of Formula III.

An oxime can be produced by any of the following processes:

(i) reacting a ketone with an aqueous solution of hydroxylamine;

(ii) reacting a ketone with ammonia and hydrogen peroxide in the presence of a catalyst such as titanosilicate;

In the production process (i) for an oxime, since hydroxylamine is unstable, a method where a hydroxylamine salt undergoes double decomposition in the presence of a ketone in a reaction vessel and then a liberated hydroxylamine and ketone are reacted is generally employed for safety operation. Here, preferably, a ketone of Formula IV and hydroxylamine are reacted in equimolar amounts.

Since hydroxylamine used in the production process (i) for an oxime is unstable, it is produced and sold as an aqueous solution of an acid salt of hydroxylamine such as hydroxylamine sulfate or hydroxylamine carbonate. Before conducting a reaction, a base such as aqueous ammonia is added to the solution to liberate hydroxylamine, which is used for the reaction. Although an aqueous solution of hydroxylamine preliminarily liberated can be fed in the production process of an oxime, generally an aqueous solution of an acid salt of hydroxylamine (preferably, hydrochloride or sulfate) and a base (preferably, aqueous ammonia) are fed into an oxime-forming reaction vessel, to liberate hydroxylamine in the reaction vessel.

The additional base is preferably selected from the group comprising of alkali metal hydroxide such as sodium hydroxide, potassium hydroxide, calcium hydroxide, strontium hydroxide, barium hydroxide or lithium hydroxide; alkali metal carbonates such as sodium carbonate, cesium carbonate, potassium carbonate or lithium carbonate; alkali metal bicarbonates such as sodium bicarbonate, cesium bicarbonate or potassium bicarbonate; alkali metal alkoxides such as sodium methoxide, potassium methoxide, sodium ethoxide, potassium ethoxide, sodium t-butoxide or potassium t-butoxide; amine bases such as triethylamine, diisopropylamine, tripropyl amine, tributyl amine, or cyclohexyl dimethyl amine; aromatic amines such as pyridine, and lutidine and the like.

In a production step of an oxime, a solvent is used. Preferably, an oxime is highly dissolvable in the solvent. A suitable solvent depends on the type of an oxime.

Generally, the reaction solvent must be inert. By "inert organic solvent" is meant an organic solvent, which under the reaction conditions of a process according to the present invention, does not react with either the reactants or the products.

In addition, as a solvent used in a production step of an oxime, a solvent which may react with a starting material during production of the oxime, even if the solvent exhibits good dissolvability of the oxime, is preferably precluded. For example, when a ketone or aldehyde is used as a solvent, it reacts with hydroxylamine to form a ketoxime or aldoxime. When a nitrile is used as a solvent, it reacts with hydroxylamine to form an amidoxime. An amide also, when being used as a solvent, forms an adduct with hydroxylamine. When an amine is used as a solvent, it reacts with a ketone to form a Schiff base. Therefore, these solvents, although these exhibit good dissolvability of an oxime, must be precluded from a solvent herein.

The reaction is preferably conducted in any suitable solvent, which may for example be selected from the group comprising of C1 to C6 halogenated hydrocarbons such as dichloromethane, dichloroethane, chloroform, carbon tetrachloride and the like; C6 to C14 aromatic hydrocarbons such as toluene, xylene, ethylbenzene, propylbenzene, butylbenzene, trimethylbenzene, tetramethylbenzene and cyclohexylbenzen, C1 to C5 alcohols such as methanol, ethanol, isopropanol, t-butanol and the like; C2 to C7 esters such as ethyl acetate, methyl acetate, isopropyl acetate and the like; nitriles such as acetonitrile, propionitrile and the like; C4 to C7 ethers, C1 to C5 carboxylic acids, water, or suitable mixtures of these solvents.

The reaction is preferably carried out at a temperature of about 0° C. to about reflux temperature of the solvent used, preferably about 20° C. to about 100° C., more preferably about 30° C. to about 80° C.; for about an hour to about 20 hours, preferably about 2 hours to about 15 hours, most preferably about 5 hours to about 12 hours.

Preferably, ketoxime is prepared by refluxing an aqueous solution of compound of formula IV with hydroxylamine hydrochloride.

Preferably, the reaction mixture is neutralized with acid, and the product is isolated, for example by filtration, extraction, and/or distillation.

Alternatively, ketoxime may be produced by applying methods known in the prior art.

For example, oximation may be efficiently carried out with $NH_2OH \cdot HCl$ under microwave irradiation. The reaction is performed in water or water-ethanol as green solvents to give in a perfect selectively with excellent yields.

Alternatively, ketoxime may be prepared by basic aluminia, CaO, and TiO2/($SO4^{2-}$) coupled with microwave irradiation under solvent-free condition.

Alternatively ZnO catalyst may be used in a microwave irradiation under solvent-free condition to prepare ketoxime.

Alternatively, the ketoxime may be prepared by simply grinding ketone with hydroxylamine hydrochloride and Bi2O3 in a mortar with a pestle at room temperature for the required period of time. This method minimizes waste disposal problems.

Ketoxime of Formula III obtained by the above processes may be optionally purified by crystallization. There are no particular restrictions to a solvent in crystallization purification of an oxime as long as it is inert to an oxime and can appropriately solve an oxime.

Ketoxime of Formula III is reacted with compound of Formula II in the presence of a suitable base, and a suitable solvent to provide Siponimod I.

The compound of Formula II can be prepared by the process described in this application or any of the processes described in the art.

The base is preferably selected from the group comprising of alkali metal hydroxide such as sodium hydroxide, potassium hydroxide, calcium hydroxide, strontium hydroxide, barium hydroxide or lithium hydroxide; alkali metal carbonates such as sodium carbonate, cesium carbonate, potassium carbonate, lithium carbonate, sodium hydrogen carbonate or potassium hydrogen carbonate; alkali metal bicarbonates such as sodium bicarbonate, cesium bicarbonate or potassium bicarbonate; alkali metal alkoxides such as sodium methoxide, potassium methoxide, sodium ethoxide, potassium ethoxide, sodium t-butoxide or potassium t-butoxide; alkali metal phosphates such as sodium hydrogen phosphate or potassium hydrogen phosphate; amine bases such as triethylamine, diisopropylamine, tripropyl amine, tributyl amine, or cyclohexyl dimethyl amine; aromatic amines such as pyridine, and lutidine; an alkali metal amides such as sodium amide, lithium diisopropylamide, lithium hexamethyldisilazide, or lithium diethylamide; an alkali metal hydrides such as sodium hydride or potassium hydride; alkyllithiums such as BuLi and N-methylpiperidine, N-methylpyrrolidine, N-methylmorpholine, or 1,8-diazabicyclo[5.4.0]undec-7-ene and the like.

The reaction is preferably conducted in any suitable solvent, which may for example be selected from the group comprising of C1 to C5 alcohols such as methanol, ethanol, isopropanol, n-propanol, n-butanol, isobutanol, t-butanol and the like; C2 to C7 esters such as ethyl acetate, methyl acetate, isopropyl acetate and the like; C4 to C7 ethers such as diethyl ether, dimethyl ether, diisopropyl ether, cyclic ethers such as THF, 1,4-dioxane; nitriles such as acetonitrile, propanonitriel; ketones such as acetone, propanone; polar aprotic solvents such as dimethylformamide (DMF), dimethylacetamide (DMA), dimethyl sulfoxide (DMSO), N-methyl pyrrolidone (NMP), sulfolane, diglyme; halogenated solvent such as chloroform, dichloromethane (MDC), dichloroethane (EDC); C6 to C14 aromatic hydrocarbons such as toluene, xylene; water, or suitable mixtures of these solvents.

The reaction is preferably carried out at a temperature of about 0° C. to about reflux temperature of the solvent used, preferably about 10° C. to about 120° C., more preferably about 30° C. to about 100° C.; for about 10 minutes to about 20 hours, preferably about 30 minutes to about 15 hours, most preferably about an hour to about 10 hours.

Preferably, Siponimod is prepared by refluxing ketoxime of formula III with compound II (wherein $X_1$ is chloro) in triethylamine and MDC.

Alternatively, Siponimod is prepared by treating ketoxime of formula III with compound II (wherein $X_1$ is chloro) in cesium carbonate in DMF at 25° C., or potassium carbonate in acetonitrile at reflux, or potassium carbonate in acetone at 35-40° C., or sodium iodide in THF at 60° C., or sodium hydroxide & TBAB in toluene at 70° C.

After completion of the reaction, the reaction mixture is added to water and the organic layer is concentrated to obtain the Siponimod of Formula I.

In another embodiment ketone of Formula IV is reacted with compound of Formula VIII to provide Siponimod I.

Preferably, compound of Formula VIII is first reacted with an acid to generate insitu, an intermediate oxime of Formula IX or salt thereof.

IX

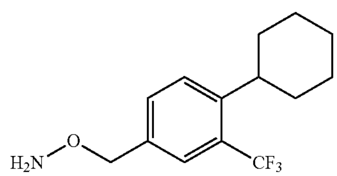

Examples of acids include but not limited to the inorganic acids such as hydrochloric acid, hydrobromic acid, nitric acid, or sulfuric acid; organic acids such as p-toluene sulfonic acid, methane sulfonic acid, ethane sulfonic acid, benzyl sulfonic acid and the like.

The reaction is preferably conducted in any suitable solvent, which may for example be selected from the group comprising of C1 to C5 alcohols such as methanol, ethanol, isopropanol, n-propanol, n-butanol, iso-butanol, t-butanol or mixture thereof and the like.

The reaction is preferably carried out at a temperature of about −20° C. to about reflux temperature of the solvent used, preferably about −15° C. to about 50° C., more preferably about 5° C. to about 40° C.; for about 15 minutes to about to about 5 hours, preferably about an hour to about 20 minutes to about 3 hours, most preferably about 25 minutes to about 2 hours.

In one embodiment oxime of Formula IX is isolated.

In another embodiment oxime of Formula IX is not isolated.

Intermediate oxime of Formula IX is then reacted with ketone of Formula IV to provide Siponimod I.

The reaction is preferably conducted in any suitable solvent, which may for example be selected from the group comprising of C1 to C5 alcohols such as methanol, ethanol, isopropanol, n-propanol, n-butanol, iso-butanol, t-butanol or mixture thereof and the like.

The reaction is preferably carried out at a temperature of about 0° C. to about reflux temperature of the solvent used, preferably about 15° C. to about 80° C., more preferably about 25° C. to about 40° C.; for about 1 hour to about 35 hours, preferably about 5 hours to about 30 hours, most preferably about 10 hours to about 25 hours.

After completion of the reaction the reaction mixture may be concentrated and the resultant suspension may be filtered or the mixture may be extracted with a suitable water immiscible solvent such as ethyl acetate or isopropyl acetate and the organic layer is concentrated to obtain the Siponimod of Formula I.

According to another embodiment of the present invention, there is provided process for the preparation of novel intermediate of Formula IV as shown in Scheme 5.

Scheme 5

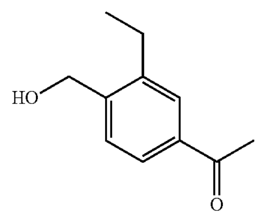

VII

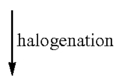

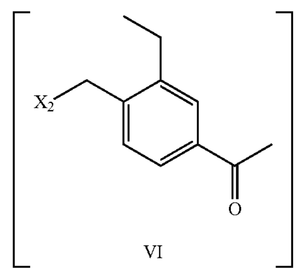

VI

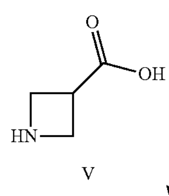

V

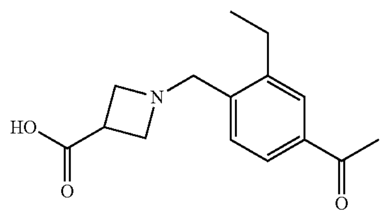

IV (Bracket indicates that the intermediate could be isolated, but is not isolated in the preferred embodiment of the present invention.)

wherein $X_2$ is a leaving group selected from halo such as chloro, bromo and iodo;

mesylate, tosylate, trilate, brosylate, phosphonate or another suitable leaving group.

Leaving groups and methods of adding them to organic compounds are well known to those of skill in the art. (See Wuts, Peter G. M. and Greene, Theodore W., *Greene's Protective Groups in Organic Synthesis,* 4'*h* Edition, Wiley, 2006, Print ISBN: 978-0-471-697S4-1, Online ISBN: 97804700S348S). Preferably $X_2$ is selected from halo, more preferably chloro and bromo.

The compound of Formula IV and VI are hitherto unreported intermediates useful in the process for the preparation of Siponimod as described herein.

In a preferred embodiment compound of Formula VII, is treated with a halogenating agent to provide compound of Formula VI.

A suitable halogenating agent is selected from chlorinating agent, brominating agent and iodinating agent. Examples of chlorinating agent are: thionyl chloride, hydrogen chloride, N-chloro succinimide, sulfonyl chlorides such as methane sulfonyl chloride, ethane sulfonyl chloride, benzene sulfonyl chloride, p-toluene sulfonyl chloride; 1, 3-Dichloro-5, 5-dimethylhydantoin, PCl3, PCl5, POCl3 or HCl gas.

Examples of brominating agents are: hydrogen bromide, POBr3, N-bromo succinimide, sulfonyl bromides, 1, 3-Dibromo-5, 5-dimethylhydantoin, PBr3, PBr5, or HBr gas.

The reaction is preferably conducted in any suitable solvent, which may for example be selected from the group comprising of halogenated hydrocarbons such as MDC, EDC, chloroform; aromatic hydrocarbons such as toluene, xylene; C1 to C5 alcohols such as methanol, ethanol, isopropanol, n-propanol, n-butanol, iso-butanol, t-butanol, nitriles such as acetonitrile, propionitrile; acetic acid, acetic anhydride, sulfuric acid, trifluoroacetic acid or mixture thereof and the like.

The reaction is preferably carried out at a temperature of about −10° C. to about reflux temperature of the solvent used, preferably about −5° C. to about 120° C., more preferably about 0° C. to about 100° C.; for about 30 minutes to about to about 10 hours, preferably about 1 hour to about 7 hours, most preferably about 2 hours to about 5 hours.

After completion of the reaction the mixture may be quenched with water and the resultant solution may be extracted with a suitable water immiscible solvent such as dichloromethane, ethyl acetate, toluene. The solvent layer may be concentrated to get the compound of formula VI.

In an embodiment compound of formula VI is reacted with compound V in the presence of a suitable base and a suitable solvent.

The base is preferably selected from the group comprising of alkali metal hydroxide such as sodium hydroxide, potassium hydroxide, calcium hydroxide, strontium hydroxide, barium hydroxide or lithium hydroxide; alkali metal carbonates such as sodium carbonate, cesium carbonate, potassium carbonate, lithium carbonate, sodium hydrogen carbonate or potassium hydrogen carbonate; alkali metal bicarbonates such as sodium bicarbonate, cesium bicarbonate or potassium bicarbonate; alkali metal alkoxides such as sodium methoxide, potassium methoxide, sodium ethoxide, potassium ethoxide, sodium t-butoxide or potassium t-butoxide; alkali metal phosphates such as sodium hydrogen phosphate or potassium hydrogen phosphate; amine bases such as triethylamine, diisopropylamine, tripropyl amine, tributyl amine, or cyclohexyl dimethyl amine; aromatic amines such as pyridine, and lutidine; an alkali metal amides such as sodium amide, lithium diisopropylamide, sodium hexamethyldisilazide, potassium hexamethyldisilazide, lithium hexamethyldisilazide, or lithium diethylamide; an alkali metal hydrides such as sodium hydride or potassium hydride; alkyllithiums such as BuLi and N-methylpiperidine, N-methylpyrrolidine, N-methylmorpholine, or 1,8-diazabicyclo[5.4.0]undec-7-ene and the like.

Generally, the reaction solvent must be inert. By "inert organic solvent" is meant an organic solvent, which under the reaction conditions of a process according to the present invention, does not react with either the reactants or the products.

A suitable inert organic solvent for use in a process according to the present invention can be selected from but are not limited to, the group comprising of polar solvents such as dimethylformamide (DMF), dimethylacetamide (DMA), dimethyl sulfoxide (DMSO), N-methyl pyrrolidone (NMP), sulfolane, diglyme; 1,4-dioxane, tetrahydrofuran, methyltetrahydrofuran, acetonitrile, acetone; C1 to C5 alcohols such as methanol, ethanol, isopropanol, n-propanol, n-butanol, iso-butanol, t-butanol; C2 to C7 esters such as ethyl acetate, methyl acetate, isopropyl acetate and the like; nitriles such as acetonitrile, propanonitrile; ketones such as acetone, propanone;

halogenated solvent such as chloroform, dichloromethane (MDC); an alkane such as hexane, heptane; dialkyl ether such as ethyl ether, diiosopropylether, t-butylmethyl ether or methyl cyclopentylether, water and other inert organic solvents known in the art or mixtures thereof.

Alternatively, the above reaction can be carried in the presence of a weaker base such as potassium carbonate, sodium carbonate, and a catalytic amount of 4-dimethyl aminopyridine (DMAP), in a ketone solvent such as acetone, methylethylketone, or cyclohexanone.

The reaction is preferably carried out at a temperature of about −40° C. to about reflux temperature of the solvent used, preferably about −30° C. to about 80° C., more preferably about −20° C. to about 70° C.; for about 1 hour to about to about 30 hours, preferably about 5 hours to about 25 hours, most preferably about 10 hours to about 20 hours.

After completion of the reaction the reaction mixture is added to water and the resultant suspension may be filtered or the mixture may be extracted with a suitable water immiscible solvent such as ethyl acetate, toluene, dichloromethane and the organic layer is concentrated to obtain the compound of formula IV. Compound IV may be optionally purified by silica gel column chromatography.

Accordingly, second embodiment of the process for the preparation of Siponimod is as shown in Scheme 6.

Scheme 6
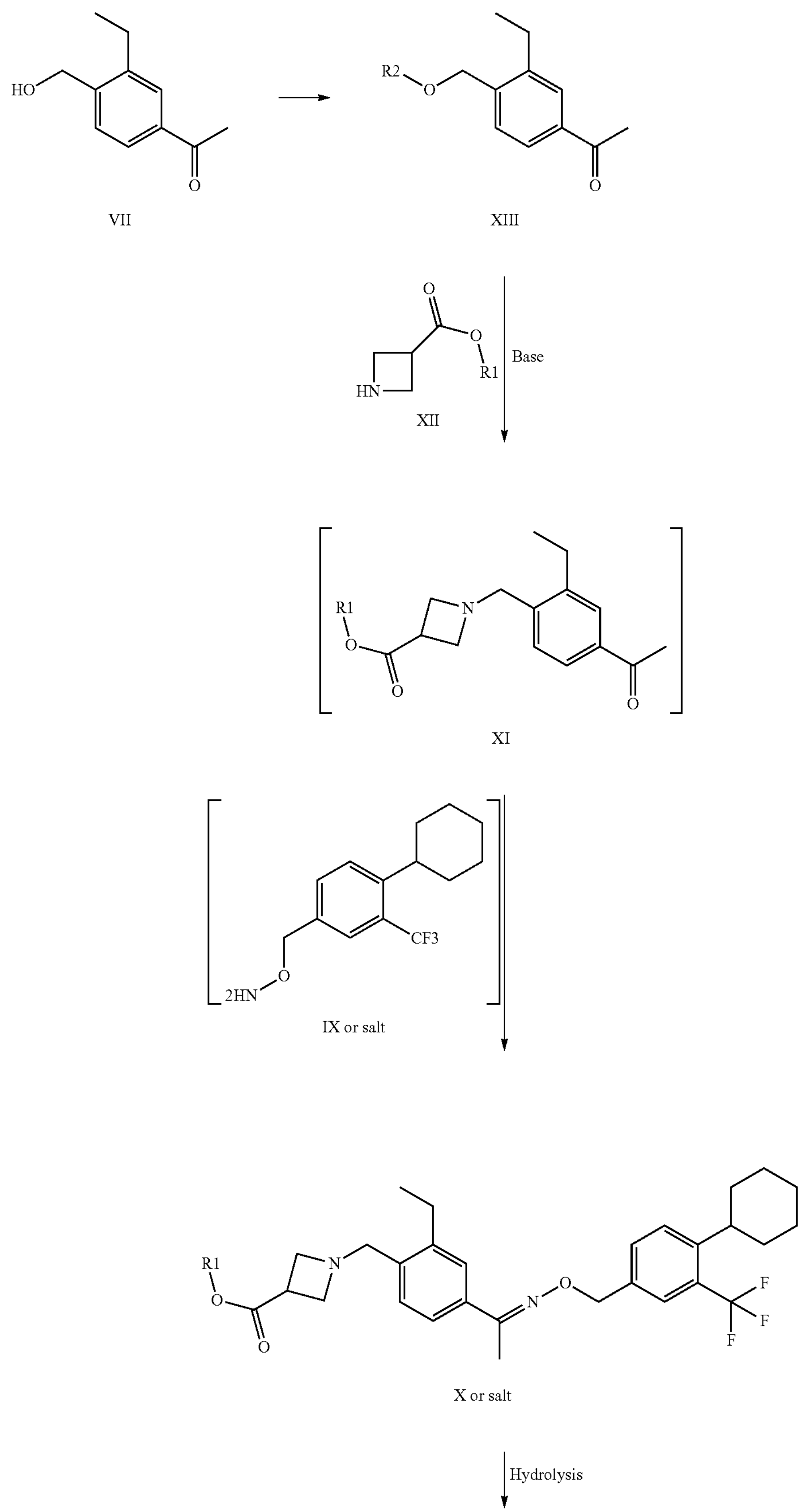
VII XIII XII XI IX or salt X or salt

-continued

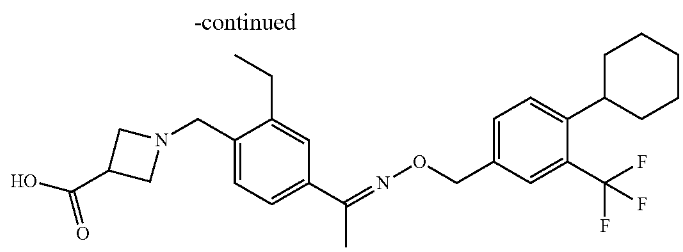

SIPONIMOD I (Bracket indicates that the intermediates could be isolated, but are not isolated in the preferred embodiment of the present invention.)

wherein R1 is C1-C4 alkyl, selected from methyl, ethyl, n-propyl, isopropyl, n-butyl and t-butyl and R2 is suitable leaving group selected from alkyl sulfonyl, aryl sulfonyl, acetyl.

The compounds of Formula IX, XI and XIII are hitherto unreported intermediates useful in the process for the preparation of Siponimod as described herein.

In a preferred embodiment compound of Formula VII is reacted with a suitable protecting group in the presence of a suitable base and solvent to provide compound of Formula XIII. Leaving groups and methods of adding them to organic compounds are well known to those of skill in the art. (See Wuts, Peter G. M. and Greene, Theodore W., *Greene's Protective Groups in Organic Synthesis,* 4'h Edition, Wiley, 2006, Print ISBN: 978-0-471-697S4-1, Online ISBN: 97804700S348S).

In an embodiment, preferred protecting groups are selected from but are not limited to, the group comprising alkyl sulfonyl halides such as methane sulfonyl chloride, ethane sulfonyl chloride, aryl sulfonyl halides such as p-toluene sulfonyl chloride, benzene sulfonyl chloride, p-bromophenyl sulfonyl chloride; p-chlorobenzene sulfonyl chloride; acetyl chloride and acetic anhydride.

The base is preferably selected from organic base and inorganic bases. Preferably base is organic base selected from the group comprising of amine bases such as triethylamine, diisopropylamine, tripropyl amine, tributyl amine, or cyclohexyl dimethyl amine; aromatic amines such as pyridine, piperidine and lutidine; an alkali metal amides such as sodium amide, lithium diisopropylamide, sodium hexamethyldisilazide, potassium hexamethyldisilazide, lithium hexamethyldisilazide, or lithium diethylamide; an alkali metal hydrides such as sodium hydride or potassium hydride; alkyllithiums such as BuLi and N-methylpiperidine, N-methylpyrrolidine, N-methylmorpholine, or 1,8-diazabicyclo[5.4.0]undec-7-ene and the like.

The reaction is preferably conducted in any suitable solvent, which may for example be selected from the group comprising of halogenated hydrocarbons such as MDC, EDC, chloroform; aromatic hydrocarbons such as toluene, xylene; aprotic solvents such as dimethylformamide (DMF), dimethylacetamide (DMA), dimethyl sulfoxide (DMSO), N-methyl pyrrolidone (NMP), sulfolane, diglyme; 1,4-dioxane, tetrahydrofuran, methyl tetrahydrofuran, acetonitrile, acetone; C2 to C7 esters such as ethyl acetate, methyl acetate, isopropyl acetate and the like; or mixture thereof and the like.

The reaction is preferably carried out at a temperature of about −10° C. to about reflux temperature of the solvent used, preferably about −5° C. to about 120° C., more preferably about 0° C. to about 100° C.; for about 1 hour to about to about 30 hours, preferably about 2 hours to about 20 hours, most preferably about 5 hours to about 10 hours.

After completion of the reaction the mixture may be quenched with water and the resultant solution may be extracted with a suitable water immiscible solvent such as dichloromethane, ethyl acetate, toluene. The solvent layer may be concentrated to get the compound of formula XIII.

In an embodiment compound of Formula XIII is reacted with compound of Formula XII (wherein R1 is methyl) in the presence of a suitable base and a suitable solvent to provide compound of Formula XI.

In an alternative embodiment compound of Formula VI is reacted with compound of Formula XII (wherein R1 is methyl) in the presence of a suitable base and a suitable solvent to provide compound of Formula XI.

The base is preferably selected from the group comprising of alkali metal hydroxide such as sodium hydroxide, potassium hydroxide, calcium hydroxide, strontium hydroxide, barium hydroxide or lithium hydroxide; alkali metal carbonates such as sodium carbonate, cesium carbonate, potassium carbonate, lithium carbonate, sodium hydrogen carbonate or potassium hydrogen carbonate; alkali metal bicarbonates such as sodium bicarbonate, cesium bicarbonate or potassium bicarbonate; alkali metal alkoxides such as sodium methoxide, potassium methoxide, sodium ethoxide, potassium ethoxide, sodium t-butoxide or potassium t-butoxide; alkali metal phosphates such as sodium hydrogen phosphate or potassium hydrogen phosphate; amine bases such as triethylamine, diisopropylamine, tripropyl amine, tributyl amine, or cyclohexyl dimethyl amine; aromatic amines such as pyridine, and lutidine; an alkali metal amides such as sodium amide, lithium diisopropylamide, sodium hexamethyldisilazide, potassium hexamethyldisilazide, lithium hexamethyldisilazide, or lithium diethylamide; an alkali metal hydrides such as sodium hydride or potassium hydride; alkyllithiums such as BuLi and N-methylpiperidine, N-methylpyrrolidine, N-methylmorpholine, or 1,8-diazabicyclo[5.4.0]undec-7-ene and the like.

Generally, the reaction solvent must be inert. By "inert organic solvent" is meant an organic solvent, which under the reaction conditions of a process according to the present invention, does not react with either the reactants or the products.

A suitable inert organic solvent for use in a process according to the present invention can be selected from but are not limited to, the group comprising of polar solvents such as dimethylformamide (DMF), dimethylacetamide (DMA), dimethyl sulfoxide (DMSO), N-methyl pyrrolidone (NMP), sulfolane, diglyme; 1,4-dioxane, tetrahydrofuran, methyltetrahydrofuran, acetonitrile, acetone; C1 to C5 alcohols such as methanol, ethanol, isopropanol, n-propanol, n-butanol, iso-butanol, t-butanol; C2 to C7 esters such as ethyl acetate, methyl acetate, isopropyl acetate and the like; nitriles such as acetonitrile, propanonitrile; ketones such as acetone, propanone;

halogenated solvent such as chloroform, dichloromethane (MDC); an alkane such as hexane, heptane; dialkyl ether such as ethyl ether, diiosopropylether, t-butylmethyl ether or methyl cyclopentylether, water and other inert organic solvents known in the art or mixtures thereof.

Alternatively, the above reaction can be carried in the presence of a weaker base such as potassium carbonate, sodium carbonate, and a catalytic amount of 4-dimethyl aminopyridine (DMAP), in a ketone solvent such as acetone, methylethylketone, or cyclohexanone.

The reaction is preferably carried out at a temperature of about 0° C. to about reflux temperature of the solvent used, preferably about 5° C. to about 100° C., more preferably about 10° C. to about 80° C.; for about 1 hour to about to about 30 hours, preferably about 5 hours to about 25 hours, most preferably about 10 hours to about 20 hours.

After completion of the reaction the reaction mixture is added to water and the resultant suspension may be filtered or the mixture may be extracted with a suitable water immiscible solvent such as ethyl acetate, toluene, dichloromethane and the organic layer is concentrated to obtain the compound of formula XI. Compound XI may be optionally purified by silica gel column chromatography.

In an embodiment, compound of Formula XI is reacted with the oxime of Formula IX or salt thereof in the presence of a suitable solvent to provide Siponimod ester of Formula X or salt thereof.

A suitable inert organic solvent for use in a process according to the present invention can be selected from but are not limited to C1-C4 alcoholic solvent such as methanol, ethanol, n-propanol, isopropanol, or n-butanol, isobutanol, t-butanol; tetrahydrofuran, methyl tetrahydrofuran, water or mixtures thereof.

The reaction is preferably carried out at a temperature of about −5° C. to about reflux temperature of the solvent used, preferably about 0° C. to about 100° C., more preferably about 10° C. to about 80° C.; for about 1 hour to about to about 40 hours, preferably about 5 hours to about 35 hours, most preferably about 10 hours to about 25 hours.

Preferably, reaction is conducted in the absence of a base.

After completion of the reaction the reaction mixture is concentrated and the resultant suspension may be filtered or the mixture may be extracted with a suitable water immiscible solvent such as ethyl acetate, toluene, dichloromethane and the organic layer is concentrated to obtain the compound of formula X or salt thereof. Compound X or salt thereof may be optionally purified by silica gel column chromatography.

In an embodiment, Siponimod ester of Formula X or salt thereof is hydrolyzed in the presence of a suitable acid or a base in the presence of a suitable solvent to provide Siponimod of Formula I.

The base is preferably selected from the group comprising of alkali metal hydroxide such as sodium hydroxide, potassium hydroxide, calcium hydroxide, strontium hydroxide, barium hydroxide or lithium hydroxide; alkali metal carbonates such as sodium carbonate, cesium carbonate, potassium carbonate, lithium carbonate, sodium hydrogen carbonate or potassium hydrogen carbonate; alkali metal bicarbonates such as sodium bicarbonate, cesium bicarbonate or potassium bicarbonate; alkali metal alkoxides such as sodium methoxide, potassium methoxide, sodium ethoxide, potassium ethoxide, sodium t-butoxide or potassium t-butoxide; alkali metal phosphates such as sodium hydrogen phosphate or potassium hydrogen phosphate; amine bases such as triethylamine, diisopropylamine, tripropyl amine, tributyl amine, or cyclohexyl dimethyl amine; aromatic amines such as pyridine, and lutidine; an alkali metal amides such as sodium amide, lithium diisopropylamide, sodium hexamethyldisilazide, potassium hexamethyldisilazide, lithium hexamethyldisilazide, or lithium diethylamide; an alkali metal hydrides such as sodium hydride or potassium hydride; alkyllithiums such as BuLi and N-methylpiperidine, N-methylpyrrolidine, N-methylmorpholine, or 1,8-diazabicyclo[5.4.0]undec-7-ene and the like.

The acid is preferably selected from the group comprising of hydrochloric acid methane sulfonic acid, oxalic acid, fumaric acid, para toluene sulfonic acid and the like.

A suitable inert organic solvent for use in a process according to the present invention can be selected from but are not limited to C1-C4 alcoholic solvent such as methanol, ethanol, n-propanol, isopropanol, or n-butanol, isobutanol, t-butanol; tetrahydrofuran, methyl tetrahydrofuran, water or mixtures thereof.

The reaction is preferably carried out at a temperature of about −10° C. to about reflux temperature of the solvent used, preferably about −5° C. to about 80° C., more preferably about 0° C. to about 60° C.; for about 1 hour to about to about 40 hours, preferably about 5 hours to about 35 hours, most preferably about 10 hours to about 25 hours.

After completion of the reaction the reaction mixture may be concentrated and the resultant suspension may be filtered or the mixture may be extracted with a suitable water immiscible solvent such as ethyl acetate or isopropyl acetate and the organic layer is concentrated to obtain the Siponimod of Formula I.

The obtained crude Siponimod may be purified using known purification techniques such as slurring and recrystallization using a suitable solvent to get pure Siponimod of Formula I or using silica gel column chromatography.

Siponimod base obtained by the processes of the present invention may be converted to the pharmaceutically acceptable salt by reacting the free base form of the compound with a pharmaceutically acceptable inorganic or organic acid.

Examples of pharmaceutically acceptable acid addition salts of Siponimod include salts with inorganic acids, such as hydrochloride, hydrobromide, nitrate and sulfate, salts with organic acids, such as acetate, adipate, fumarate, hemifumarate, malate, maleate, benzoate, citrate, malate, methanesulfonate, oxalate, tartrate, glutarate and benzenesulfonate salts, or, when appropriate, salts with metals such as sodium, potassium, calcium and aluminium, salts with amines, such as triethylamine and salts with dibasic amino acids, such as lysine. In a preferred embodiment Siponimod is Siponimod hemifumarate.

According to another embodiment of the present invention, there is provided process for the preparation of Intermediate oxime of Formula IX or of Formula IV as shown in Scheme 7.

Scheme 7

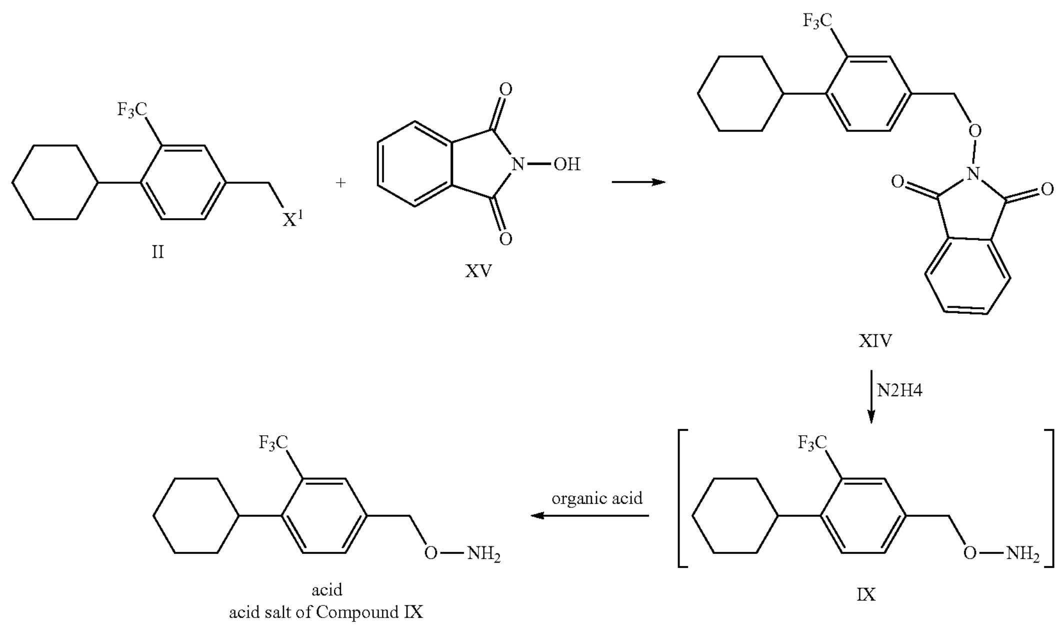

II XV XIV IX acid
acid salt of Compound IX (Bracket indicates that the intermediate could be isolated, but is not isolated in the preferred embodiment of the present invention.)

wherein $X_1$ is a leaving group selected from bromo, chloro, iodo and fluoro, preferably bromo or chloro.

The compound of Formula IX is hitherto unreported intermediate useful in the process for the preparation of Siponimod as described herein.

In an embodiment compound II is reacted with n-hydroxy phthalimide of Formula XV in the presence of a suitable base and suitable solvent to provide compound of Formula XIV.

The base is preferably selected from the group comprising of alkali metal hydroxide such as sodium hydroxide, potassium hydroxide, calcium hydroxide, strontium hydroxide, barium hydroxide or lithium hydroxide; alkali metal carbonates such as sodium carbonate, cesium carbonate, potassium carbonate, lithium carbonate, sodium hydrogen carbonate or potassium hydrogen carbonate; alkali metal bicarbonates such as sodium bicarbonate, cesium bicarbonate or potassium bicarbonate; alkali metal alkoxides such as sodium methoxide, potassium methoxide, sodium ethoxide, potassium ethoxide, sodium t-butoxide or potassium t-butoxide; alkali metal phosphates such as sodium hydrogen phosphate or potassium hydrogen phosphate; amine bases such as triethylamine, diisopropylamine, tripropyl amine, tributyl amine, or cyclohexyl dimethyl amine; aromatic amines such as pyridine, and lutidine; an alkali metal amides such as sodium amide, lithium diisopropylamide, sodium hexamethyldisilazide, potassium hexamethyldisilazide, lithium hexamethyldisilazide, or lithium diethylamide; an alkali metal hydrides such as sodium hydride or potassium hydride; alkyllithiums such as BuLi and N-methylpiperidine, N-methylpyrrolidine, N-methylmorpholine, or 1,8-diazabicyclo[5.4.0]undec-7-ene and the like.

Generally, the reaction solvent must be inert. By "inert organic solvent" is meant an organic solvent, which under the reaction conditions of a process according to the present invention, does not react with either the reactants or the products.

A suitable inert organic solvent for use in a process according to the present invention can be selected from but are not limited to, the group comprising of polar solvents such as dimethylformamide (DMF), dimethylacetamide (DMA), dimethyl sulfoxide (DMSO), N-methyl pyrrolidone (NMP), sulfolane, diglyme; 1,4-dioxane, Tetrahydrofuran (THF), methyltetrahydrofuran, acetonitrile, acetone; C1 to C5 alcohols such as methanol, ethanol, isopropanol, n-propanol, n-butanol, iso-butanol, t-butanol; C2 to C7 esters such as ethyl acetate, methyl acetate, isopropyl acetate and the like; nitriles such as acetonitrile, propanonitrile; ketones such as acetone, propanone;

halogenated solvent such as chloroform, dichloromethane (MDC); an alkane such as hexane, heptane; dialkyl ether such as ethyl ether, diisopropylether, t-butylmethyl ether or methyl cyclopentylether, water and other inert organic solvents known in the art or mixtures thereof.

The reaction is preferably carried out at a temperature of about 20° C. to about reflux temperature of the solvent used, preferably about 30° C. to about 100° C., more preferably about 40° C. to about 80° C.; for about 30 minutes to about to about 10 hours, preferably about 1 hour to about 5 hours.

After completion of the reaction the reaction mixture is cooled to the room temperature and solids are isolated by filtration to obtain the compound of formula XIV.

Compound XIV may be optionally purified by known techniques.

In an embodiment, compound of Formula XIV is reacted with hydrazine or salts thereof of suitable solvent to provide compound of Formula IX.

Examples of hydrazine salts include but not limited to the hydrazine hydrochloride, hydrazine sulfate and the like.

The reaction is preferably conducted in any suitable solvent, which may for example be selected from the group comprising of THF, DMF, DMSO, C1 to C5 alcohols such as methanol, ethanol, isopropanol, n-propanol, n-butanol, iso-butanol, t-butanol or mixture thereof and the like.

The reaction is preferably carried out at a temperature of about 0° C. to about reflux temperature of the solvent used, preferably about 10° C. to about 50° C., more preferably about 20° C. to about 40° C.; for about 1 hour to about 10 hours, preferably about 2 hours to 8 hours, most preferably about 3 hours to about 6 hours.

After completion of the reaction, the inorganics are separated and clear filtrate is concentrated to obtain oxime of Formula IX.

In one embodiment oxime of Formula IX is isolated.

In another embodiment oxime of Formula IX is not isolated and converted to the salt.

Example of acid addition salts include but not limited to the salts with organic acids, such as oxalate, tartrate, citrate, malate, acetate, adipate, fumarate, hemifumarate, malate, maleate, benzoate, methanesulfonate, glutarate and benzenesulfonate salts, salts with inorganic acids, such as hydrochloride, hydrobromide, nitrate and sulfate. In a preferred embodiment oxime of Formula IX is converted to oxalate salt.

In another embodiment, the invention provides crystalline polymorphs of Siponimod fumarate.

As polymorphic forms are reliably characterized by peak positions in the X-ray diffractogram, the polymorphs of the present invention have been characterized by powder X-ray diffraction spectroscopy which produces a fingerprint of the particular crystalline form. Measurements of 2θ values are accurate to within ±0.2 degrees. All the powder diffraction patterns were measured on a PANalytical X'Pert3 X-ray powder diffractometer with a copper-K-α radiation source.

The invention further provides processes for the preparation of polymorphs.

Thus, in first aspect, the present invention provides the crystalline Siponimod fumarate, wherein the said fumarate is referred to as "Form-C1".

The crystalline Form-C1 is relatively stable towards moisture and humidity, thereby representing a crystalline form of Siponimod fumarate, thus enhancing the efficacy of the parent molecule in lower doses.

The crystalline Form-C1 according to the present invention may be characterized by powder X-ray diffraction.

Crystalline Form-C1 may be characterized by having an XRPD diffractogram comprising peaks at 7.23, 12.34, 12.70, 16.49 and 17.78±0.2°2θ. The XRPD diffractogram may comprise further peaks at 11.75, 13.65, 15.67, 18.58 and 26.05±0.2° 2θ. The XRPD diffractogram may be as depicted in FIG. 1.

The crystalline Form-C1 according to the present invention may also be characterized as having a DSC spectrum exhibiting three endothermic peaks, melting with a first endotherm onset at around 65.50±5° C. and a peak maximum at 78.61±5° C., second endotherm onset at around 95.79±5° C. and a peak maximum at 105.66±5° C. and third endotherm onset at around 115.75±5° C. and a peak maximum at 134.22±5° C.

Figure 2:
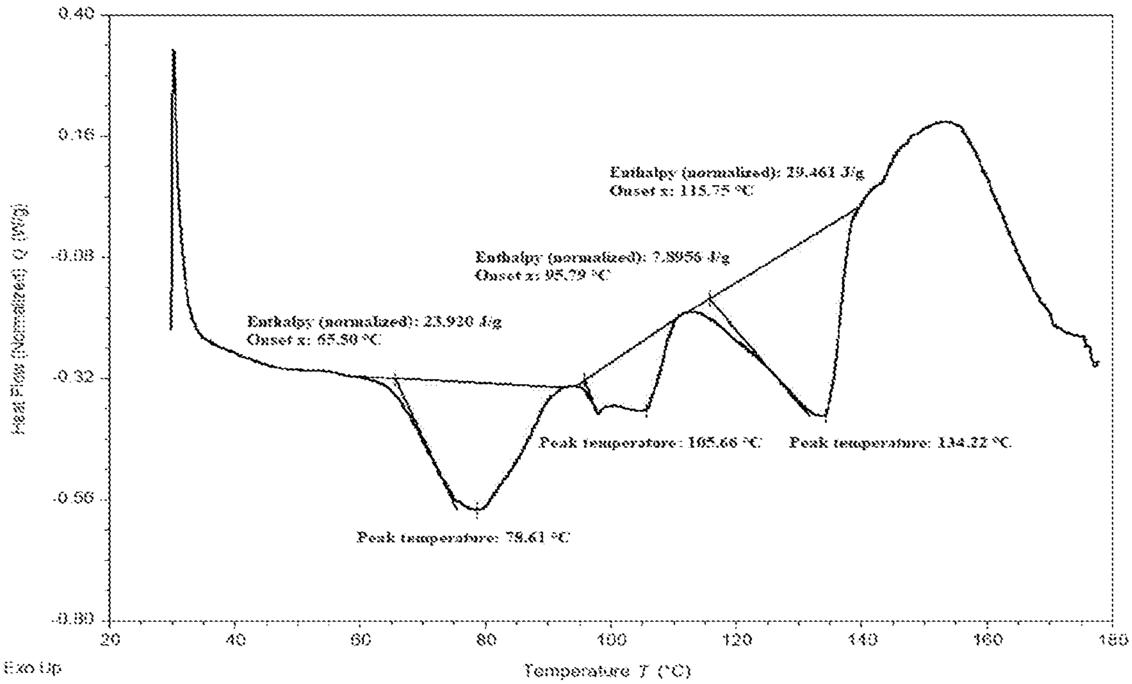
FIG. 2 depicts DSC of crystalline Siponimod fumarate Form-C1

In an embodiment, crystalline Siponimod fumarate Form-C1 may be characterized by having a DSC spectrum as shown in FIG. 2.

Figure 3:
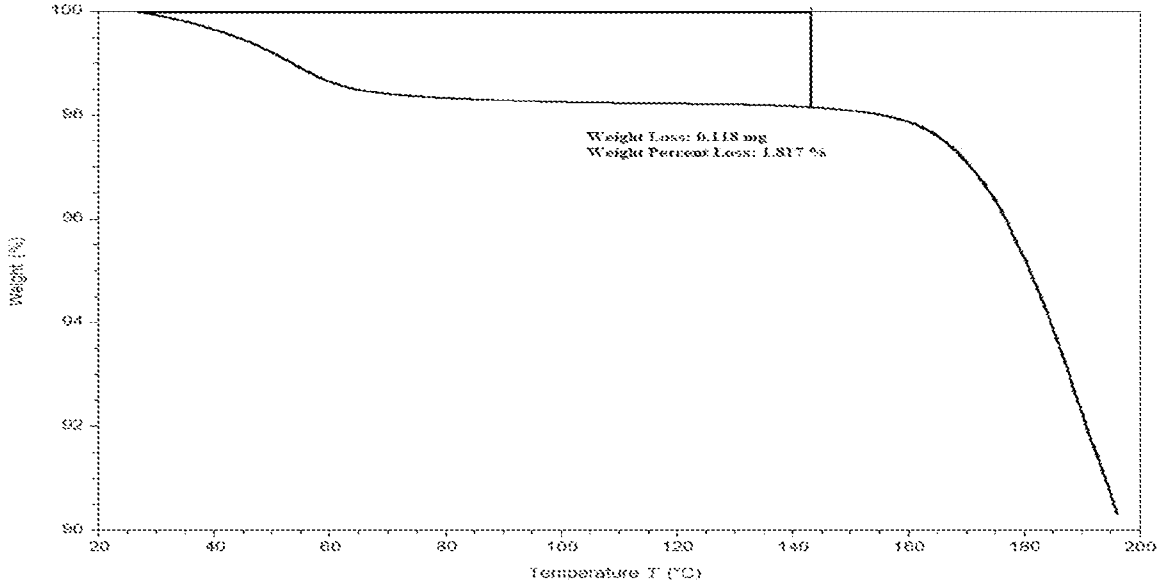
FIG. 3 depicts TGA of crystalline Siponimod fumarate Form-C1

The crystalline Siponimod fumarate Form-C1 may also be characterized by having a TGA thermogram substantially as depicted in FIG. 3.

TGA data indicated little or no weight loss up to 140° C. A small weight loss, typically about 1.8%, was observed between 30° C. and 145° C., probably associated with inclusion of the water in the crystals. The TGA analysis indicates the crystalline Siponimod fumarate Form-C1 may be a hydrate form.

Those skilled in the art would recognize that Form C1 may be further characterized by other methods including, but not limited to IR, solid state NMR, intrinsic dissolution and Raman spectroscopy.

According to another aspect of the present invention, there is provided a process for preparing crystalline Form C1 of Siponimod fumarate, the process comprising:

a) suspending Siponimod fumarate in a non polar solvent selected from but not limited to hexane, heptane, toluene, xylene and the like
b) stirring for at least 20-25 hours at 25-30° C.;
c) isolating the precipitated crystalline Form C1; and
d) drying under reduced pressure at 40-50° C., preferably at 30-50° C. for at least 3-4 hours.

In a second aspect, the present invention provides the crystalline Siponimod fumarate, wherein the said fumarate is referred to as "Form C2".

The crystalline Form C2 is relatively stable towards moisture and humidity, thereby representing a crystalline form of Siponimod fumarate, thus enhancing the efficacy of the parent molecule in lower doses.

The crystalline Form C2 according to the present invention may be characterized by powder X-ray diffraction.

Figure 4:
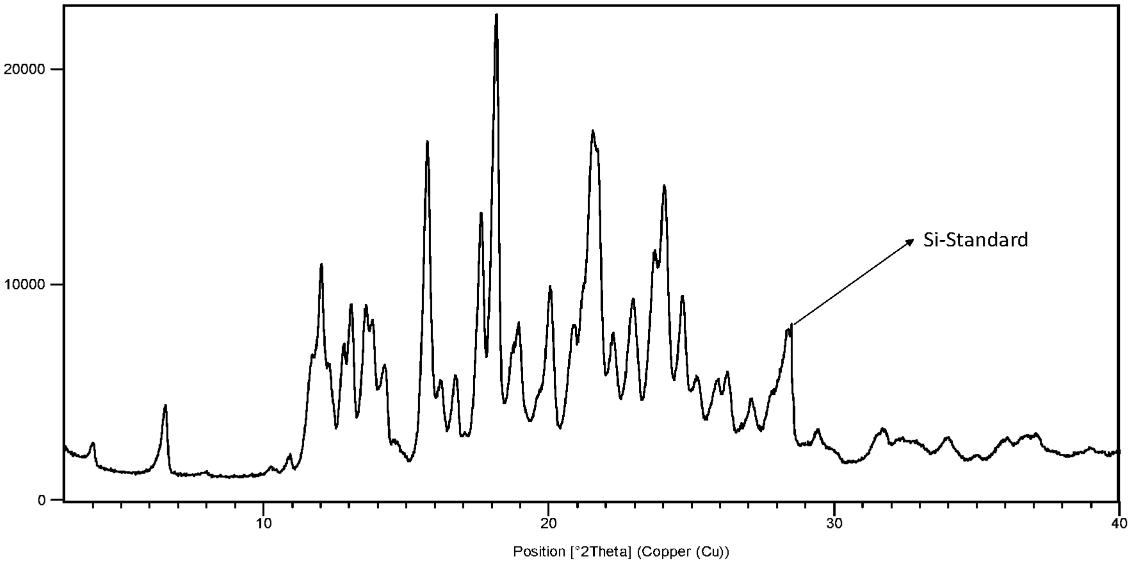
FIG. 4 depicts X-Ray Powder Diffraction (XRPD) pattern of crystalline Siponimod fumarate Form-C2

Crystalline Form C2 may be characterized by having an XRPD diffractogram comprising peaks at 6.46, 11.96, 15.66, 17.54 and 18.08±0.2°2θ. The XRPD diffractogram may comprise further peaks at 3.94, 13.53, 16.64, 22.85 and 24.60±0.2°2θ. The XRPD diffractogram may be as depicted in FIG. 4.

The crystalline Form C2 according to the present invention may also be characterized as having a DSC spectrum exhibiting two endothermic peaks, melting with a first endotherm onset at around 88.67±5° C. and a peak maximum at 98.72±5° C., and second endotherm onset at around 124.58±5° C. and a peak maximum at 138.57±5° C.

Figure 5:
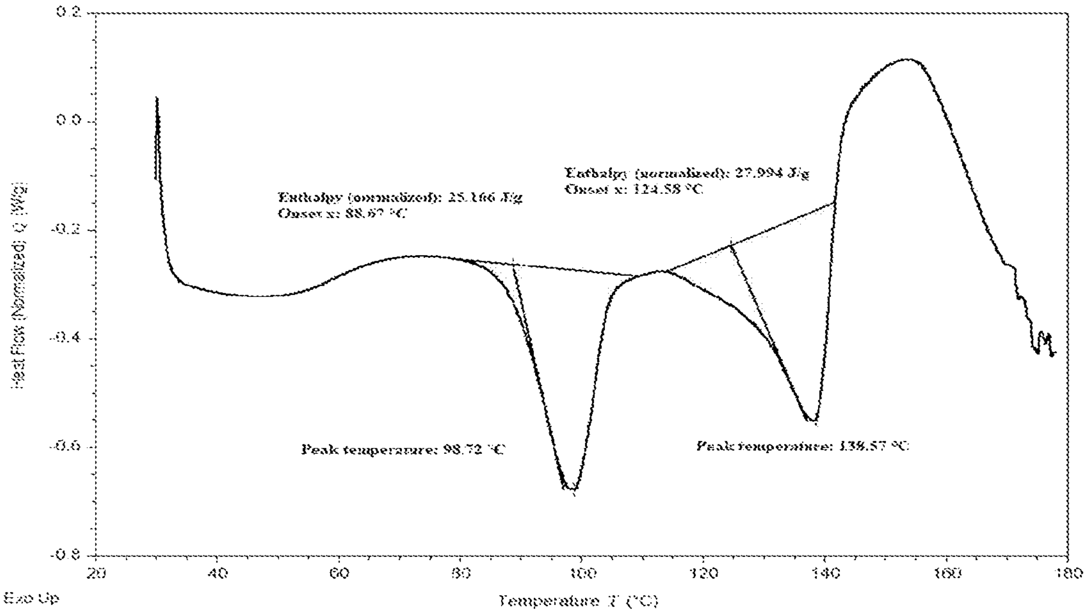
FIG. 5 depicts DSC of crystalline Siponimod fumarate Form-C2

In an embodiment, crystalline Siponimod fumarate Form-C2 may be characterized by having a DSC spectrum as shown in FIG. 5.

Figure 6:
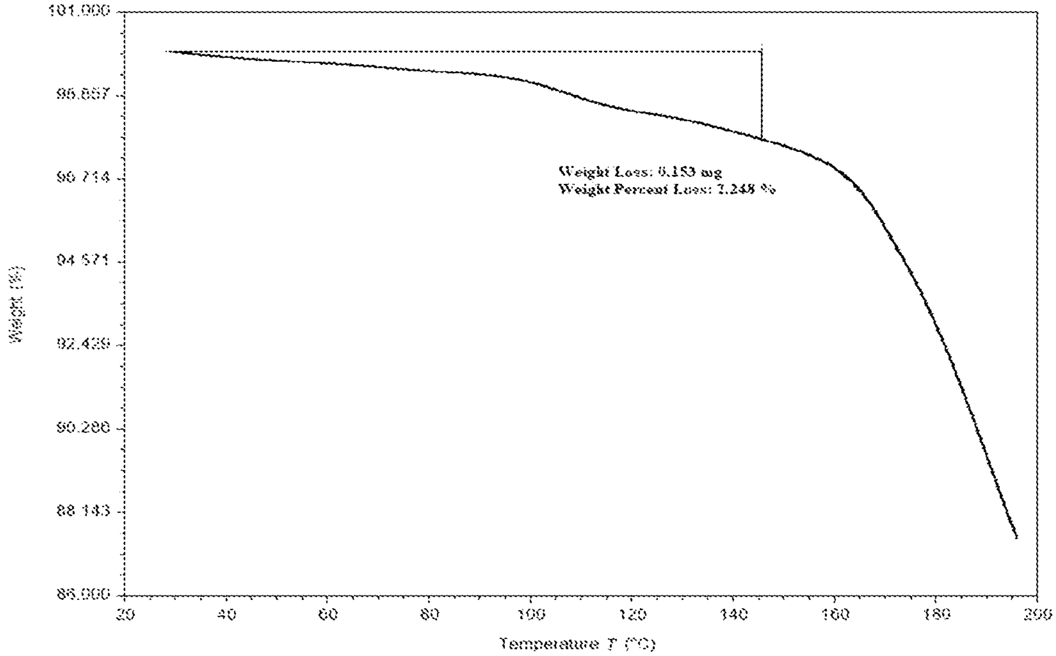
FIG. 6 depicts TGA of crystalline Siponimod fumarate Form-C2

The crystalline Siponimod fumarate Form-C2 may also be characterized by having a TGA thermogram substantially as depicted in FIG. 6.

TGA data indicated little or no weight loss up to 140° C. A small weight loss, typically about 2.24%, was observed between 30° C. and 145° C., probably associated with inclusion of the crystallizing solvent in the crystals. The TGA analysis indicates the crystalline Siponimod fumarate Form-C2 may be a solvate of N-methyl pyrrolidone (NMP).

Those skilled in the art would recognize that Form C2 may be further characterized by other methods including, but not limited to IR, solid state NMR, intrinsic dissolution and Raman spectroscopy.

According to another aspect of the present invention, there is provided a process for preparing crystalline Form C2 of Siponimod fumarate, the process comprising:

a) dissolving Siponimod fumarate in a polar aprotic solvent selected from but not limited to acetone, acetonitrile, dimethylformamide (DMF), dimethylacetamide (DMA), dimethyl sulfoxide (DMSO), N-methyl pyrrolidone (NMP), sulfolane, diglyme; 1,4-dioxane, tetrahydrofuran, methyltetrahydrofuran;
b) adding water to the mixture;
c) stirring for at least 2-5 hours at 25-30° C.;
d) isolating the precipitated crystalline Form C2; and
e) drying under reduced pressure at 40-70° C., preferably at 50-60° C. for at least 3-5 hours.

In a third aspect, the present invention provides the crystalline Siponimod fumarate, wherein the said fumarate is referred to as "Form-C3".

The crystalline Form-C3 is relatively stable towards moisture and humidity, thereby representing a crystalline form of Siponimod fumarate, thus enhancing the efficacy of the parent molecule in lower doses.

The crystalline Form-C3 according to the present invention may be characterized by powder X-ray diffraction.

Figure 7:
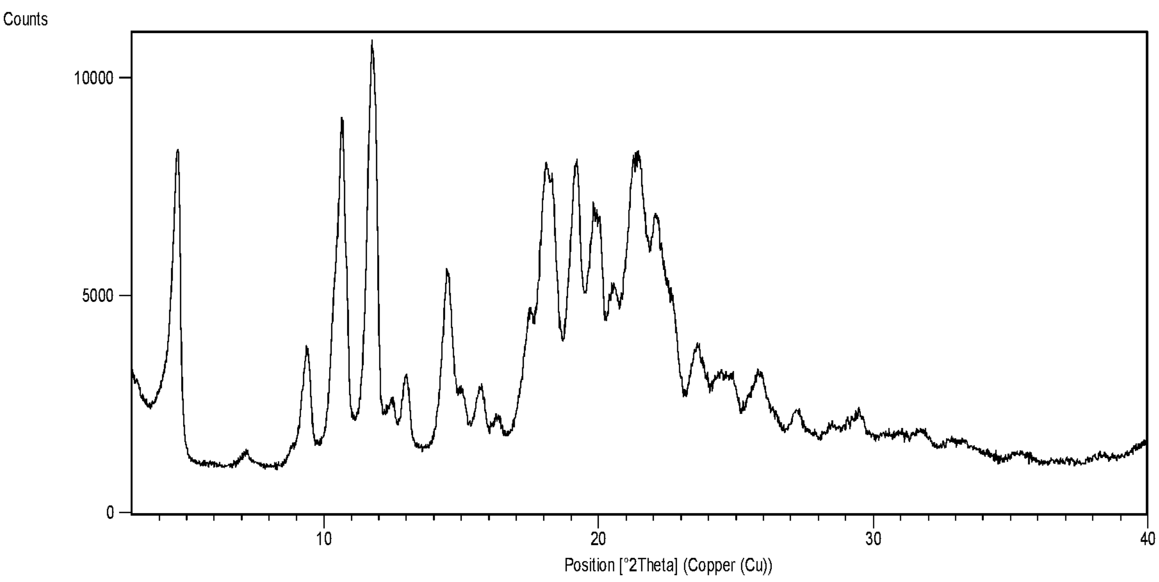
FIG. 7 depicts X-Ray Powder Diffraction (XRPD) pattern of crystalline Siponimod fumarate Form-C3

Crystalline Form-C3 may be characterized by having an XRPD diffractogram comprising peaks at 4.67, 9.37, 10.68, 11.72, 14.50 and 19.17±0.2° 2θ. The XRPD diffractogram may be as depicted in FIG. 7.

The crystalline Form-C3 according to the present invention may also be characterized as having a DSC spectrum exhibiting single endothermic peak, melting with an endotherm onset at around 130.18±5° C. and a peak maximum at 134.76±5° C.

Figure 8:
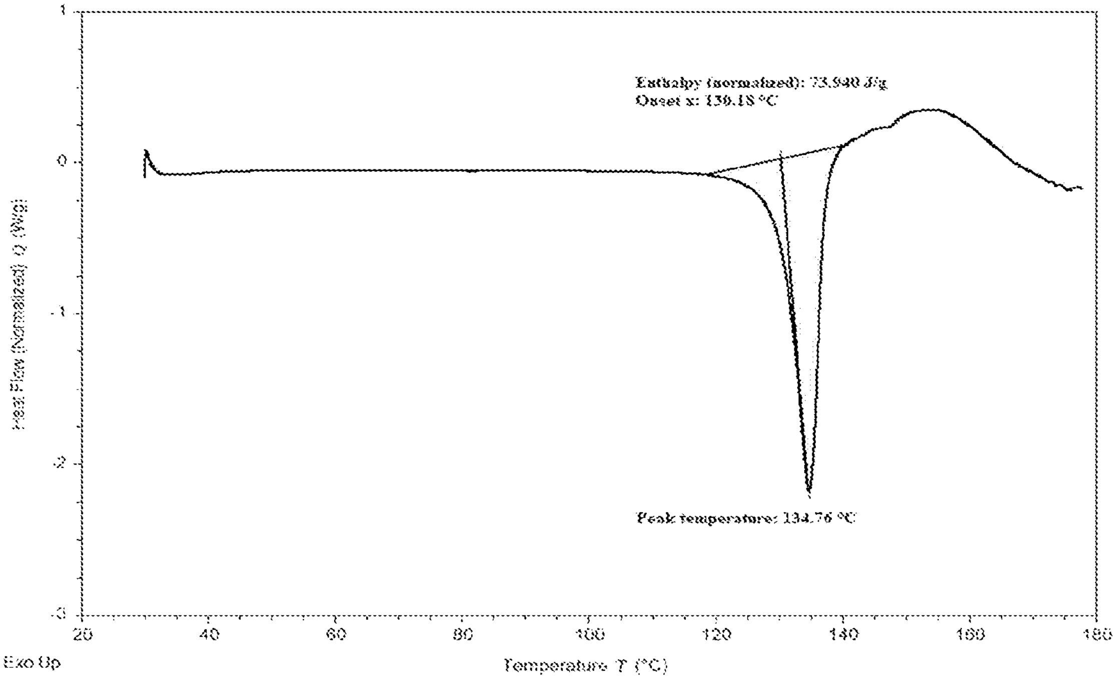
FIG. 8 depicts DSC of crystalline Siponimod fumarate Form-C3

In an embodiment, crystalline Siponimod fumarate Form-C3 may be characterized by having a DSC spectrum as shown in FIG. 8.

Figure 9:
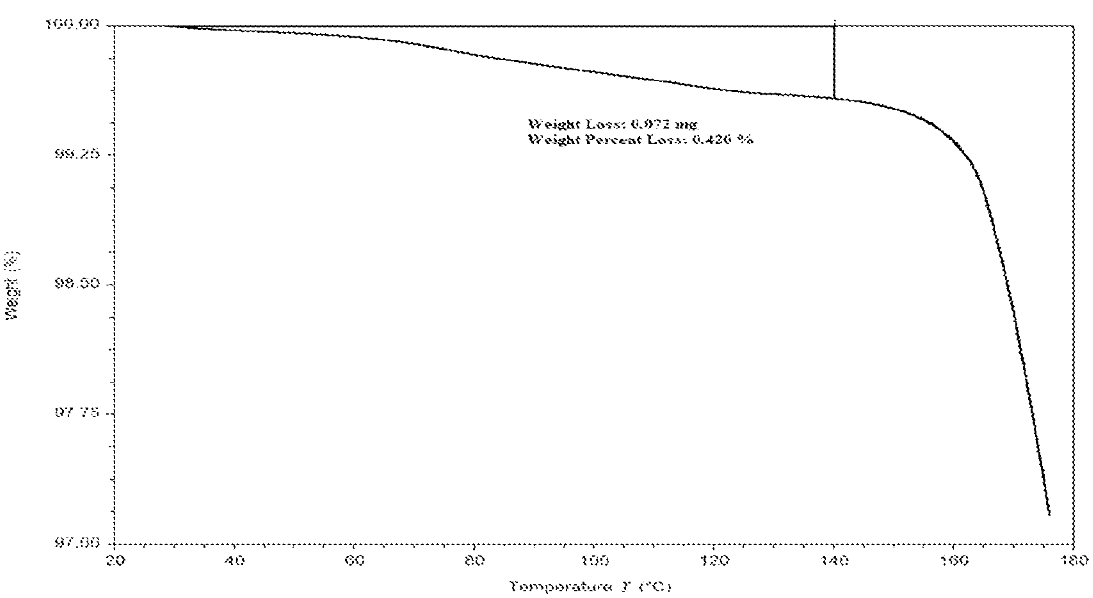
FIG. 9 depicts TGA of crystalline Siponimod fumarate Form-C3

The crystalline Siponimod fumarate Form-C3 may also be characterized by having a TGA thermogram substantially as depicted in FIG. 9.

TGA data indicated little or no weight loss up to 140° C. A small weight loss, typically about 0.42%, was observed between 30° C. and 145° C., probably associated with inclusion of the crystallizing solvent in the crystals. The TGA analysis indicates the crystalline Siponimod fumarate Form-C3 is the anhydrous form.

Figure 10:
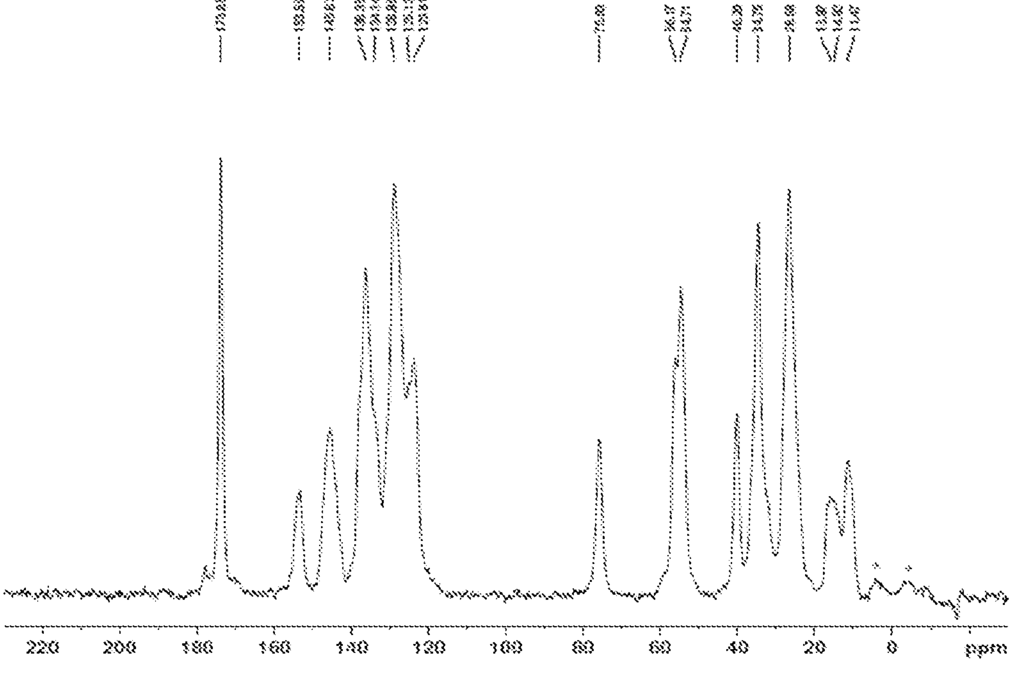
FIG. 10 depicts Solid state $^{13}C$ NMR of crystalline Siponimod fumarate Form-C3

In an embodiment, crystalline Siponimod fumarate Form-C3 may be characterized by having a Solid-state $^{13}C$ NMR spectra as shown in FIG. 10.

Figure 11:
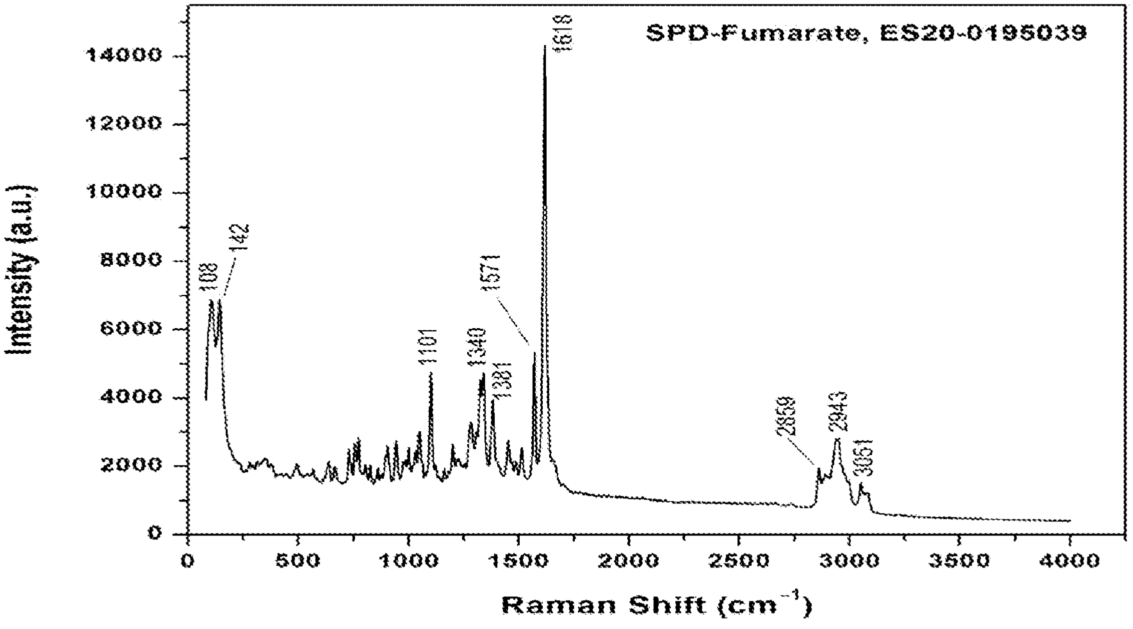
FIG. 11 depicts Raman spectra of crystalline Siponimod fumarate Form-C3

In an embodiment, crystalline Siponimod fumarate Form-C3 may be characterized by having a Raman spectra as shown in FIG. 11.

Those skilled in the art would recognize that Form-C3 may be further characterized by other methods including, but not limited to IR, intrinsic dissolution and Raman spectroscopy.

Preferably the crystalline Form-C3 of Siponimod fumarate, has a crystalline purity of at least 80%, more preferably at least 90%, more preferably at least 95%, most preferably at least 99% by weight.

According to another aspect of the present invention, there is provided a process for preparing crystalline Form-C3 of Siponimod fumarate, the process comprising:

a) treating Siponimod fumarate in a suitable first organic solvent or mixture of organic solvents;
b) treating with a second organic solvent or mixture of organic solvents;
c) isolating the precipitated crystalline Form-C3; and
d) drying the solids.

The Siponimod fumarate may be in any polymorphic form or in a mixture of any polymorphic forms. Preferably, Siponimod fumarate is in the amorphous form. The starting material Siponimod fumarate can be obtained by the process of the present invention or any methods known in the art, such as the one described in U.S. Pat. No. 9,604,914 B2 which is incorporated herein by reference.

In an embodiment first and second organic solvents used in the preparation of Form C3, are different. Preferably, first organic solvent is polar solvent and second organic solvent is non-polar solvent.

In one embodiment treating includes mixing, dissolving, slurring or suspending the Siponimod fumarate in the first solvent.

Suitable first solvent includes polar solvent and non polar solvent. Polar solvents include but are not limited to C1-C4 alcohol such as methanol, ethanol, isopropanol, n-propanol, t-butanol, iso-butanol, trifluoro ethanol and the like; ketones such as acetone, butanone, and methyl isobutyl ketone, methyl isobutyl ketone, methyl vinyl ketone; nitriles such as acetonitrile, propionitrile; polar aprotic solvents such as dimethyl formamide, dimethyl sulfoxide, tetrahydrofuran, methyltetrahydrofuran, 1,4-dioxane, sulfolane, diglyme, trioxane, N-methyl pyrrolidone and dimethyl acetamide;

halogenated hydrocarbons such as MDC, EDC, chloroform, carbon tetrachloride; aliphatic hydrocarbons such as heptane, hexane, aromatic hydrocarbons such as toluene, xylene, chlorobenzene and the like or mixture thereof.

Preferably, Siponimod fumarate is treated with first solvent at about −20° C. to about reflux temperature of the solvent used.

Preferably, the solution is maintained at about 40° C. to about 60° C.

Suitable second solvent includes polar solvent and non-polar solvent. Polar solvents include but are not limited to water, ethers such as dimethyl ether, diethyl ether, diisopropyl ether, t-butyl methyl ether, dibutyl ether, tetrahydrofuran, 1,4-dioxane; ketones such as isobutyl methyl ketone, ethyl methyl ketone, acetone, methyl t-butyl ketone, methyl isopropyl ketone, methyl amyl ketone, and diisobutyl ketone. Non-polar solvents include but are not limited to hexane, heptane, toluene, xylene, tetraline, chlorobezene and the like or mixture thereof.

Prior to the addition, preferably, second solvent is maintained at about −20° C. to about 30° C., preferably at about −15° C. to about 15° C.

Prior to the addition, optionally Form-C3 seeds are charged to the second solvent solution to form the seed slurry.

In one embodiment, solution of first solvent is added to the either solution or slurry of second solvent while stirring.

In another embodiment, solution or slurry of second solvent is added to the solution of first solvent while stirring.

Typically, after the addition, a slurry is obtained. The obtained slurry is preferably maintained while stirring. Preferably, stirring is done for a period of about 15 minutes to about 10 hours, more preferably, for about 30 minutes to about 5 hours at about −15° C. to about 15° C., preferably at about −10° C. to about 15° C., more preferably at −5° C. to about 5° C.

Typically, a precipitate is formed in the solution. In an embodiment, isolation include but not limited to filtration by gravity or suction, centrifugation, decantation, and any other known techniques in the art. Preferably, removing the precipitate is done by filtration.

Preferably, the obtained precipitate is dried to obtain a solid form. In an embodiment, drying can be carried out in a tray dryer, vacuum oven, air oven, cone vacuum dryer, rotary vacuum dryer, fluidized bed dryer, spin flash dryer, flash dryer, or the like.

The drying may be done at a temperature of about 30° C. to about 60° C., preferably at about 40° C. to about 50° C. Preferably, drying is performed for about 1 hour to about 10 hours, more preferably, for about 2 to about 5 hours.

Crystalline forms of Siponimod fumarate of the present invention may be used in the purification of Siponimod hemifumarate and in the preparation of other crystalline forms.

In yet another embodiment, the invention provides novel synergistic pharmaceutical compounds of Siponimod with group of organic acids also recalled as "co-former". The pharmaceutical compound may be a co-crystal The novel pharmaceutical compounds are relatively stable towards the moisture and humidity, thereby representing an amorphous or a crystalline form of pharmaceutical compound, thus enhancing the efficacy of the parent molecule in lower doses.

In an embodiment "co-former" is selected from one or more pharmaceutically acceptable organic acids.

Organic acids are preferably selected from but not limited to the group comprising of adipic acid and glutaric acid.

The present co-crystal, typically comprises Siponimod and the organic acid within the same crystalline phase in a molar ratio ranging from 1:0.25 to 1:1.2.

In a first aspect of the invention is provided a co-crystal of Siponimod and adipic acid. In some embodiments, co-crystal is hemi adipic acid co-crystal. In some embodiments, co-crystal is mono adipic acid co-crystal.

The adipic acid co-crystal can, in certain embodiments, be in hydrated or solvated form. Preferably, the co-crystal comprises Siponimod and adipic acid within the same crystalline phase in a molar ratio ranging from 1:0.25 to 1:0.75. More preferably the co-crystal comprises Siponimod and adipic acid within the same crystalline phase in a molar ratio of 1:0.5.

The crystalline Siponimod adipic acid co-crystal is referred to as "Form C1".

In an embodiment, Siponimod adipic acid co-crystal Form C1, can be characterized as having peaks in X-ray powder diffraction patterns obtained therefrom. For example, co-crystal can be characterized by an X-ray powder diffraction pattern having peaks at one or more of the following 2-theta diffraction angles: 4.97, 6.50, 9.58, 13.03, 16.79, 19.58 and 21.85±0.2° 2θ.

Figure 12:
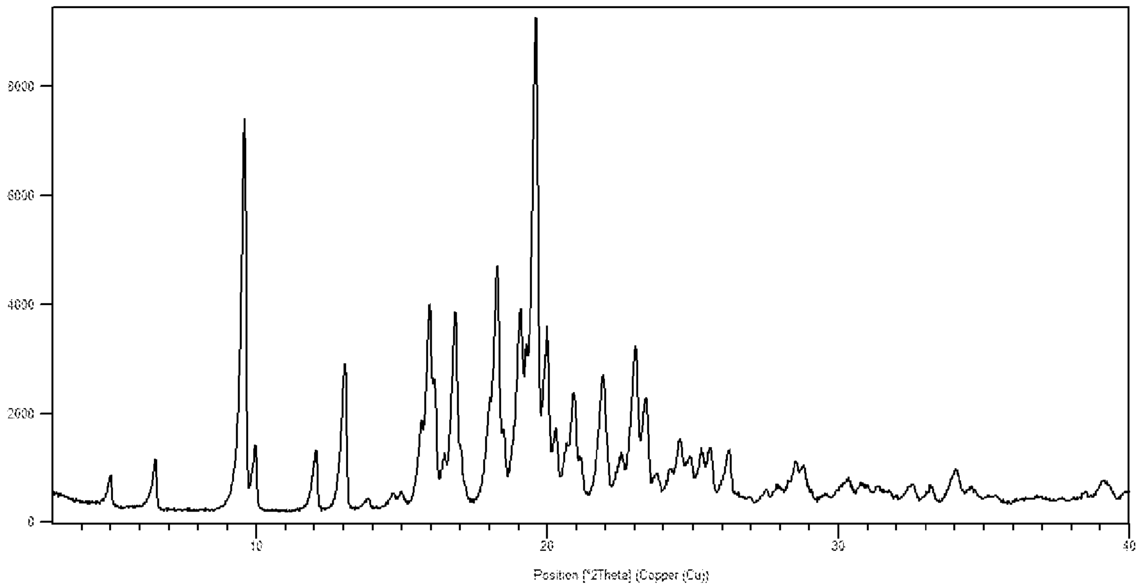
FIG. 12 depicts X-Ray Powder Diffraction (XRPD) pattern of Siponimod adipic acid co-crystal Form-C1

In another embodiment, Siponimod adipic acid co-crystal Form C1, is characterized by having an XRD pattern as shown in FIG. 12.

The Siponimod adipic acid co-crystal Form-C1, according to the present invention may also be characterized as having a DSC spectrum exhibiting single endothermic peak, melting with an endotherm onset at around 123.48±5° C. and a peak maximum at 129.48±5° C.

Figure 13:
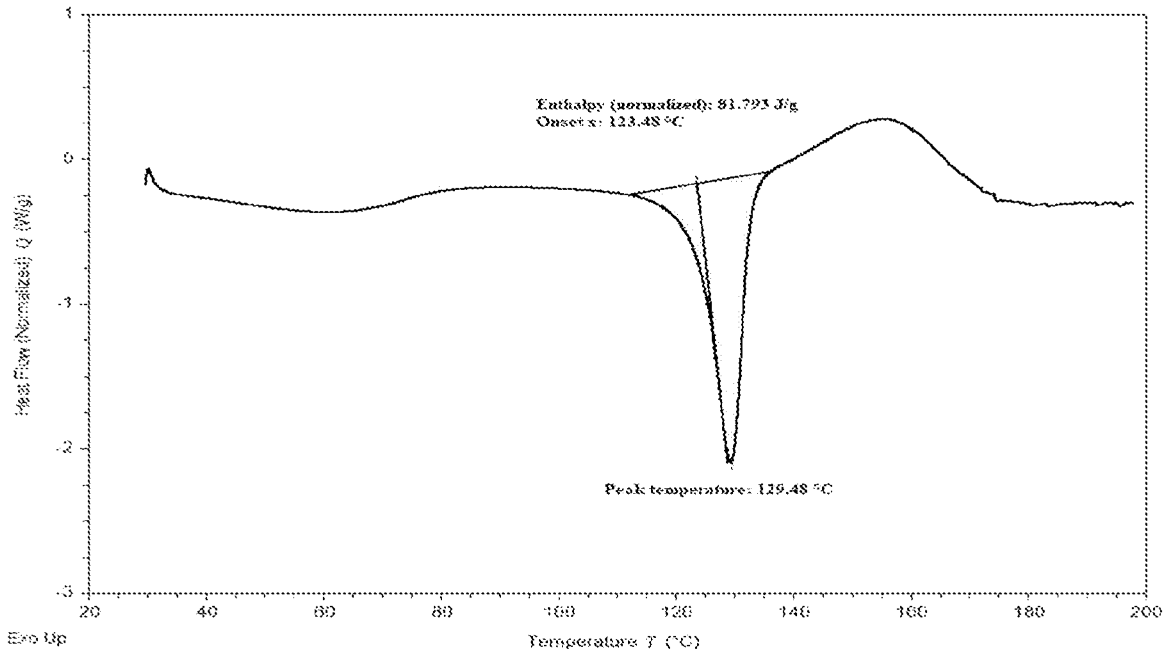
FIG. 13 depicts DSC of crystalline Siponimod adipic acid co-crystal Form-C1

In an embodiment, Siponimod adipic acid co-crystal Form-C1 may be characterized by having a DSC spectrum as shown in FIG. 13.

Figure 14:
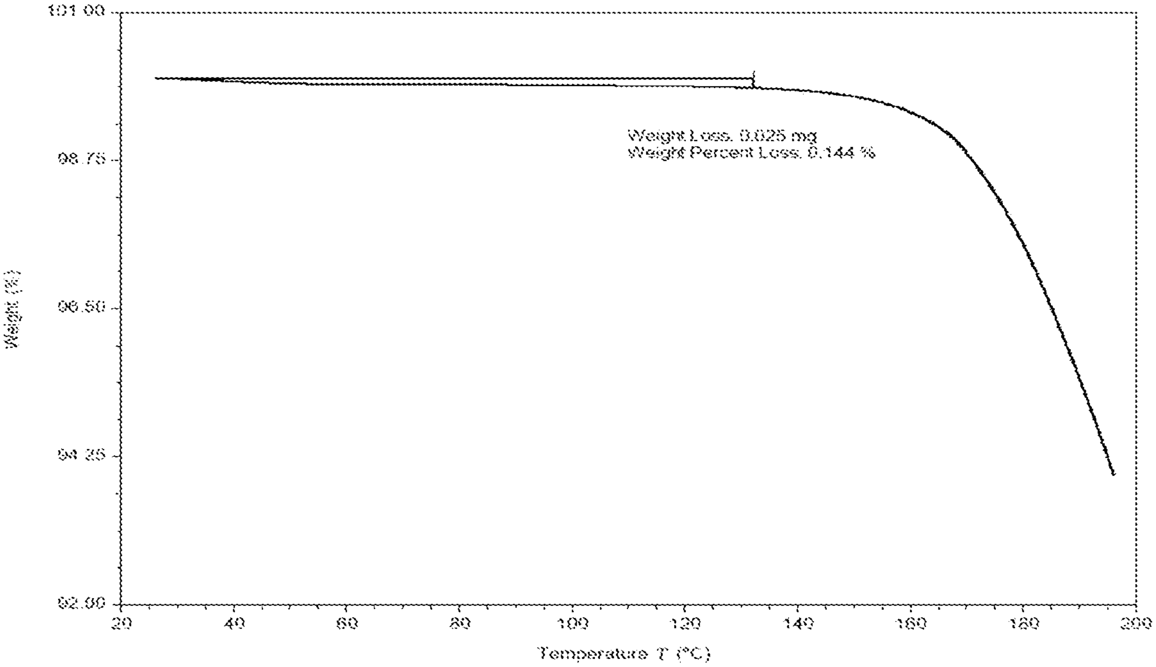
FIG. 14 depicts TGA of crystalline Siponimod adipic acid co-crystal Form-C1

The Siponimod adipic acid co-crystal Form-C1 may also be characterized by having a TGA thermogram substantially as depicted in FIG. 14.

TGA data indicated little or no weight loss up to 130° C. A small weight loss, typically about 0.144%, was observed between 30° C. and 135° C., probably associated with inclusion of the crystallizing solvent in the crystals. The TGA analysis indicates the Siponimod adipic acid co-crystal Form-C1 is the anhydrous form.

Figure 15:
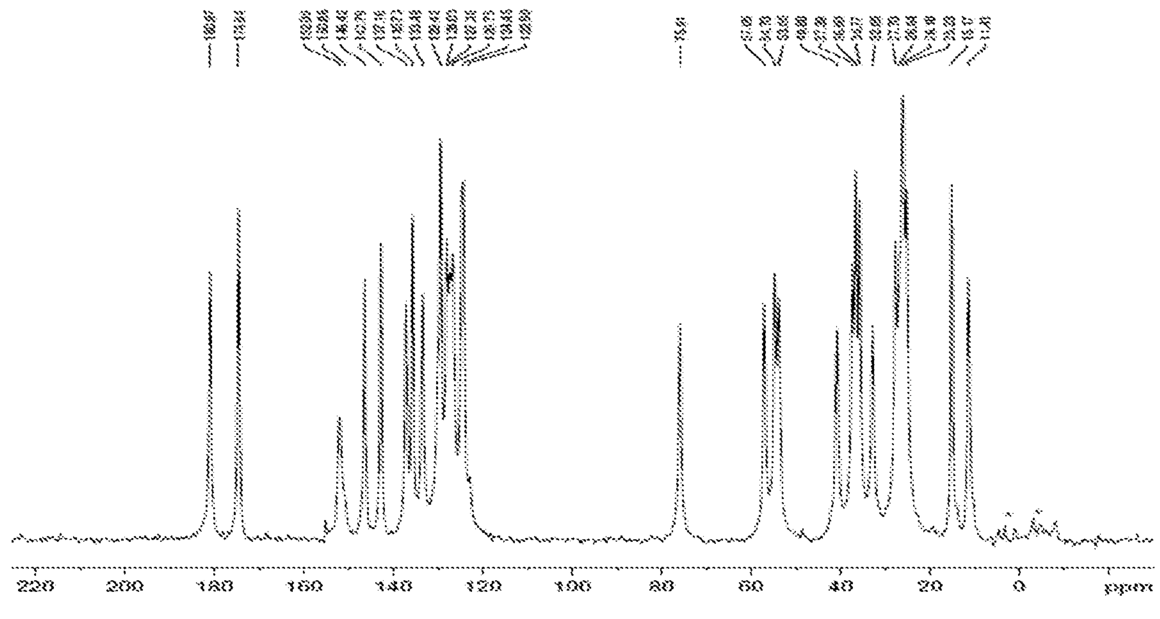
FIG. 15 depicts Solid state $^{13}C$ NMR of crystalline Siponimod adipic acid co-crystal Form-C1

In an embodiment Siponimod adipic acid co-crystal Form-C1 may be characterized by having a Solid-state $^{13}C$ NMR spectra as shown in FIG. 15.

Figure 16:
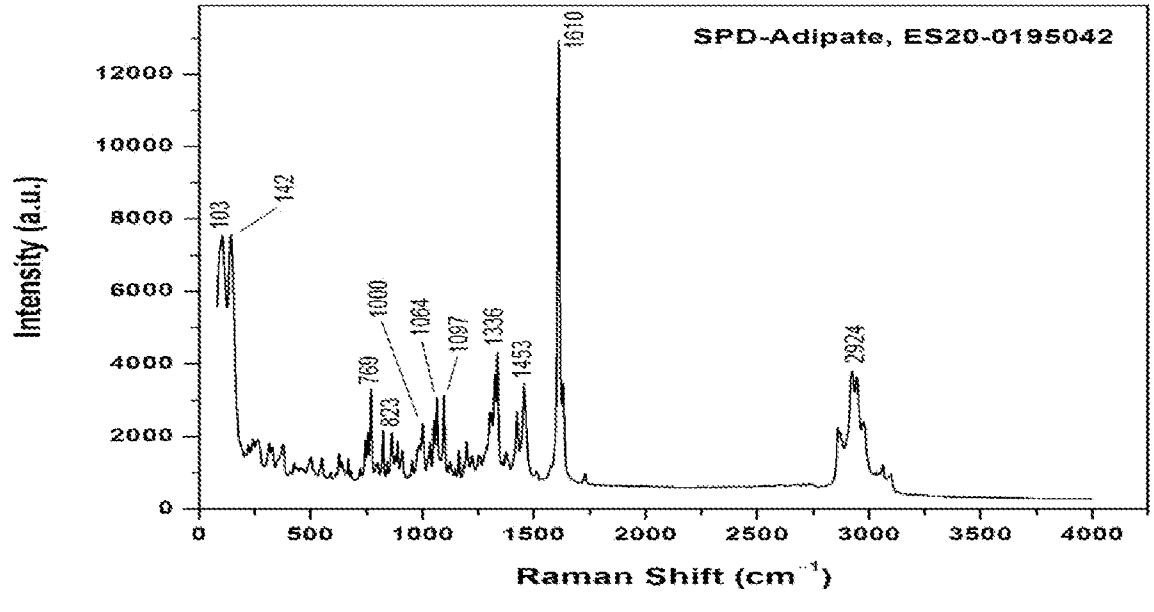
FIG. 16 depicts Raman spectra of crystalline Siponimod adipic acid co-crystal Form-C1

In an embodiment, Siponimod adipic acid co-crystal Form-C1 may be characterized by having a Raman spectra as shown in FIG. 16.

In an embodiment, Oak Ridge Thermal Ellipsoid Plot (ORTEP) of the Siponimod adipic acid co-crystal Form-C1 was drawn with ORTEP-3, v.2.02. The ellipsoids are at 50% probability.

Figure 17:
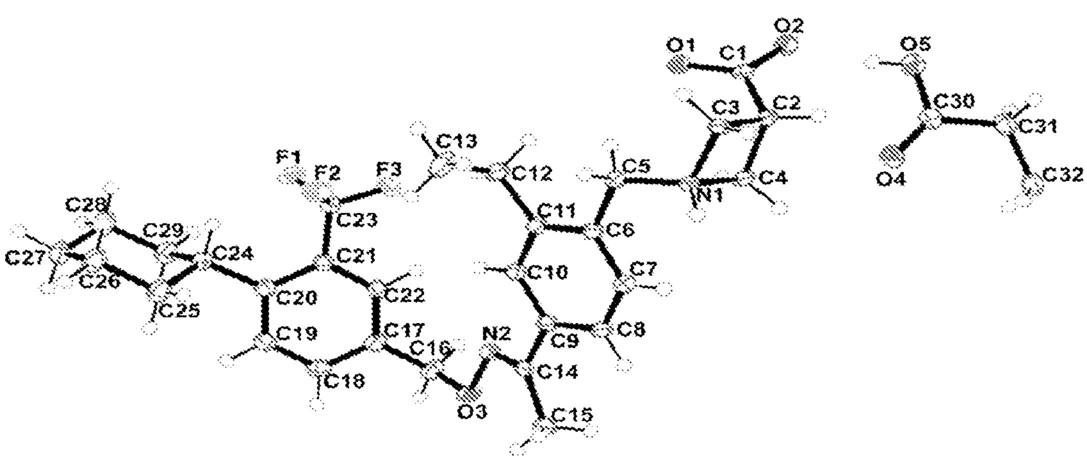
FIG. 17 depicts an ORTEP representation of crystalline Siponimod adipic acid co-crystal Form-C1

In an embodiment, an ORTEP drawing of the Siponimod adipic acid co-crystal Form-C1 is shown in FIG. 17.

A summary of the crystal data and crystallographic data collection parameters are provided in Table 1 below.

TABLE 1

| Crystallographic parameters | Siponimod Adipic acid co-crystal Form-C1 |
|---|---|
| Chemical formula | C32 H40 F3 N2 O5 |
| Asymmetric unit | C29 H35 F3 N2 O3, C3 H5 O2 |
| Formula weight | 589.66 |
| Crystal system | triclinic |
| Space group | P −1 |
| T [K] | 100 |
| a [Å] | 5.87360 (10) |
| b [Å] | 14.3533 (3) |
| c [Å] | 19.2507 (4) |
| α [°] | 110.386 (2) |
| β [°] | 95.759 (2) |
| γ [°] | 90.638 (2) |
| Z | 2 |
| V[$Å^3$] | 1511.76 (5) |
| Unique reflns. | 5287 |
| Observed reflns. | 4902 |
| $R_1$ [I > 2(I)] | 0.0373 |
| $wR_2$ (all) | 0.0961 |
| Goodness-of-fit | 1.033 |

In a second aspect of the invention is provided a co-crystal of Siponimod and glutaric acid. In some embodiments, co-crystal is hemi glutaric acid co-crystal. In some embodiments, co-crystal is mono glutaric acid co-crystal. The glutaric acid co-crystal can, in certain embodiments, be in hydrated or solvated form. Preferably, the co-crystal comprises Siponimod and glutaric acid within the same crystalline phase in a molar ratio ranging from 1:0.5 to 1:1.2. More preferably the co-crystal comprises Siponimod and glutaric acid within the same crystalline phase in a molar ratio of 1:0.5.

The crystalline Siponimod glutaric acid co-crystal is referred to as "Form C1".

In an embodiment, Siponimod glutaric acid co-crystal Form C1, can be characterized as having peaks in X-ray powder diffraction patterns obtained therefrom. For example, co-crystal can be characterized by an X-ray powder diffraction pattern having peaks at one or more of the following 2-theta diffraction angles: 6.45, 9.85, 10.15, 12.93, 17.24 and 23.40±0.2° 2θ.

Figure 18:
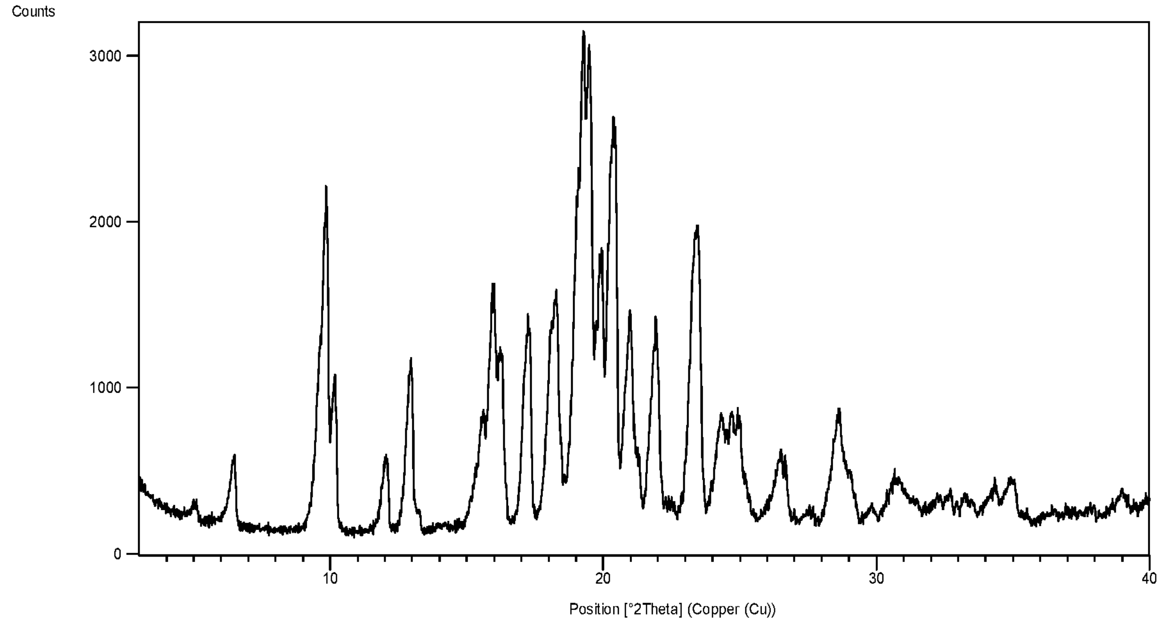
FIG. 18 depicts X-Ray Powder Diffraction (XRPD) pattern of Siponimod glutaric acid co-crystal Form-C1

In another embodiment, Siponimod glutaric acid co-crystal Form-C1, is characterized by having an XRD pattern as shown in FIG. 18.

The Siponimod glutaric acid co-crystal Form-C1, according to the present invention may also be characterized as having a DSC spectrum exhibiting single endothermic peak, melting with an endotherm onset at around 102.93±5° C. and a peak maximum at 108.01±5° C.

Figure 19:
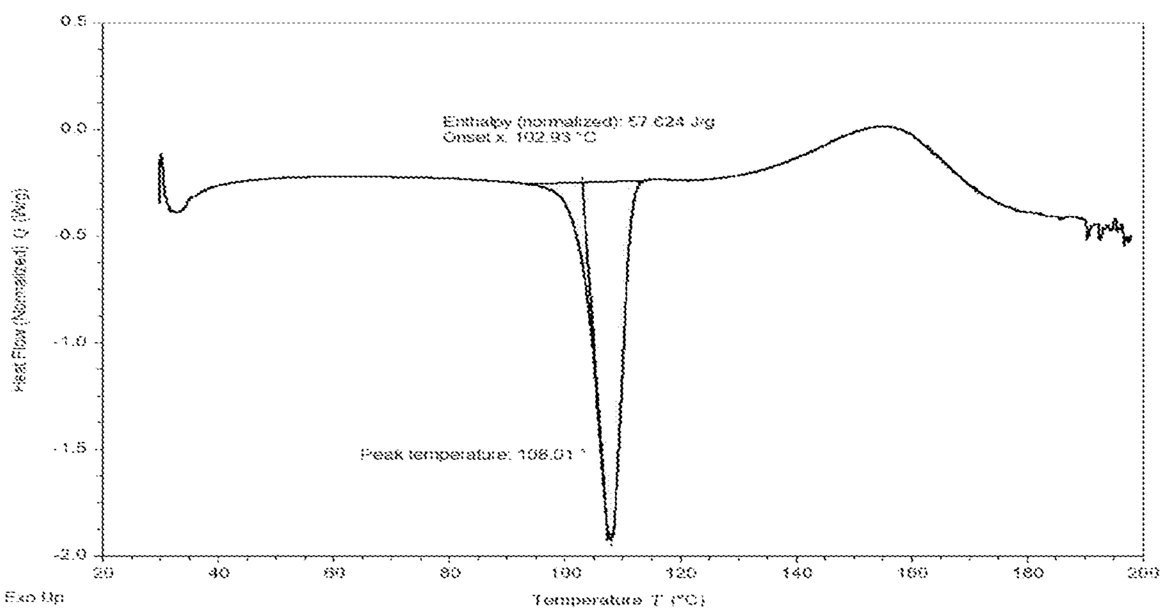
FIG. 19 depicts DSC of crystalline Siponimod glutaric acid co-crystal Form-C1

In an embodiment, Siponimod glutaric acid co-crystal Form-C1 may be characterized by having a DSC spectrum as shown in FIG. 19.

Figure 20:
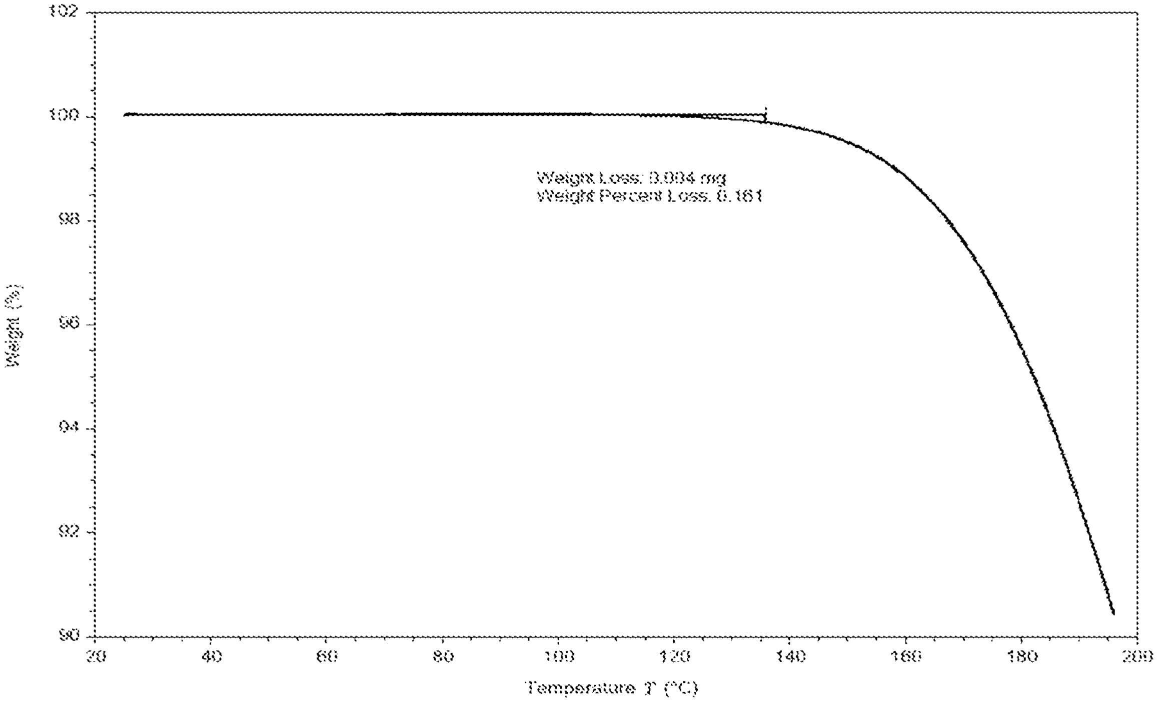
FIG. 20 depicts TGA of crystalline Siponimod glutaric acid co-crystal Form-C1

The Siponimod glutaric acid co-crystal Form-C1 may also be characterized by having a TGA thermogram substantially as depicted in FIG. 20.

TGA data indicated little or no weight loss up to 130° C. A small weight loss, typically about 0.161%, was observed between 30° C. and 140° C., probably associated with inclusion of the crystallizing solvent in the crystals. The TGA analysis indicates the Siponimod glutaric acid co-crystal Form-C1 is the anhydrous form.

According to another aspect of the present invention, there is provided a process for preparing Siponimod co-crystal, the process comprising, a) dissolving Siponimod and the corresponding organic acid in a suitable first organic solvent or mixture of organic solvents at a temperature of 25° C. to the reflux temperature of the solvent used;

b) removing the solvent;

c) stirring the residue in a second organic solvent or mixture of organic solvents for at least 1 hour to 30 hours at 25-30° C.;

d) isolating the precipitated Siponimod and organic acid co-crystal and e) drying at 30-60° C., preferably at 40-50° C. for at least 1 hour to 10 hours.

The Siponimod may be in any polymorphic form or in a mixture of any polymorphic forms. The starting material Siponimod can be obtained by the process of the present invention or any methods known in the art, such as the one described in U.S. Pat. No. 7,939,519 B2 which is incorporated herein by reference.

In an embodiment, organic solvents are selected from but not limited to the group comprising of C1 to C5 alcohols such as methanol, ethanol, isopropanol, t-butanol and the like; nitriles such as acetonitrile, propionitrile and the like; C1 to C6 halogenated hydrocarbons such as dichloromethane, dichloroethane, chloroform, carbon tetrachloride and the like; C6 to C14 aromatic hydrocarbons such as toluene, xylene, ethylbenzene, propylbenzene, butylbenzene, trimethylbenzene, tetramethylbenzene and cyclohexylbenzen, C2 to C7 esters such as ethyl acetate, methyl acetate, isopropyl acetate and the like; C4 to C7 ethers such as dimethyl ether, diethyl ether, ethyl methyl ether; cyclic ether such as tetrahydrofuan, 1,4-dioxane; aromatic ethers such as diphenyl ether; DMF, DMSO, or suitable mixtures of these solvents.

In an embodiment, removal of solvent include but not limited to evaporation, flash evaporation, simple evaporation, rotational drying, spray drying, agitated thin-film drying, Rotary vacuum paddle dryer, agitated nutsche filter drying, pressure nutsche filter drying, freeze-drying or any other suitable technique known in the art. In an embodiment solvent may be removed at normal pressure or under reduced pressure.

In an embodiment, isolation include but not limited to filtration by gravity or suction, centrifugation, decantation, and any other known techniques in the art.

In an embodiment, drying can be carried out in a tray dryer, vacuum oven, air oven, cone vacuum dryer, rotary vacuum dryer, fluidized bed dryer, spin flash dryer, flash dryer, or the like.

The invention is further defined by reference to the following examples. It will be apparent to those skilled in the art that many modifications, both to materials and methods, may be practiced without departing from the scope of the invention.

EXAMPLES

Example 1: Preparation of Siponimod

Example A: Synthesis of 1-(4-(chloromethyl)-3-ethylphenyl) ethan-1-one (Compound VI)

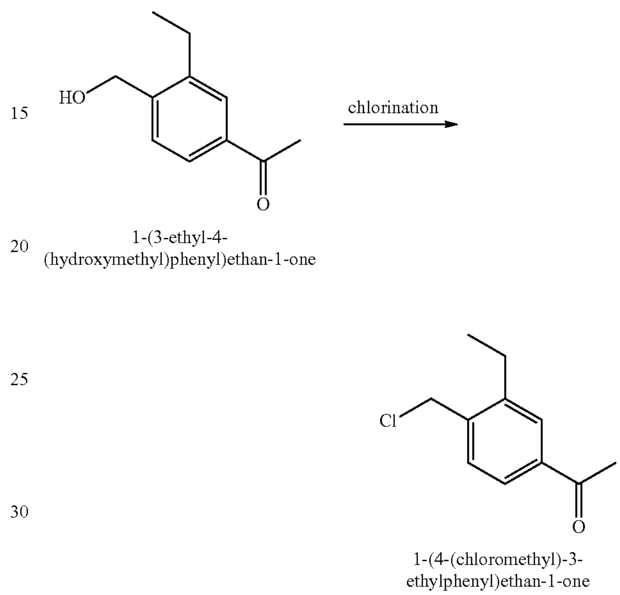

1-(3-ethyl-4-(hydroxymethyl)phenyl)ethan-1-one 1-(4-(chloromethyl)-3-ethylphenyl)ethan-1-one To a stirred solution of 1-(3-ethyl-4-(hydroxymethyl) phenyl)ethan-1-one (Compound VII) (10 g) in methylene dichloride (100 ml) and dimethyl formamide (1 ml) was added thionyl chloride (15 ml). The reaction mixture was stirred for 1 hr at room temperature. The reaction mixture washed with water. The organic layer was washed with brine solution and dried over anhydrous sodium sulfate. The organic layer was concentrated under reduced pressure at 40° C. to yield 1-(4-(chloromethyl)-3-ethylphenyl) ethan-1-one (Compound VI) as yellow oil.

Example B: Synthesis of 1-(4-acetyl-2-ethylbenzyl)azetidine-3-carboxylic acid (Compound IV)

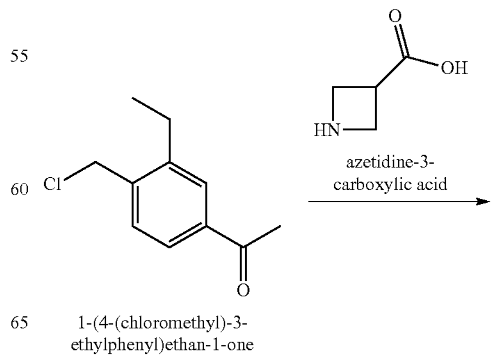

azetidine-3-carboxylic acid 1-(4-(chloromethyl)-3-ethylphenyl)ethan-1-one

-continued

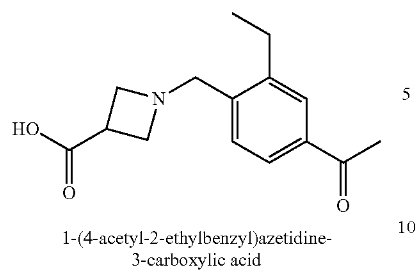

1-(4-acetyl-2-ethylbenzyl)azetidine-3-carboxylic acid

To a stirred solution of 1-(4-(chloromethyl)-3-ethylphenyl)ethan-1-one (Compound VI) (10 g) and azetidine-3-carboxylic acid (Compound V) (5 g) in methylene dichloride (100 ml), was added triethyl amine (5 ml) at room temperature. The reaction mixture was stirred for overnight at room temperature. The reaction mixture washed with water. The organic layer was washed with brine solution and dried over anhydrous sodium sulfate. The organic layer was concentrated under reduced pressure at 40° C. The residue was purified by silica gel column chromatography to yield 1-(4-acetyl-2-ethylbenzyl)azetidine-3-carboxylic acid (Compound IV).

Example C: Synthesis of 1-(2-ethyl-4-(1-(hydroxyimino)ethyl)benzyl)azetidine-3-carboxylic acid (Compound III)

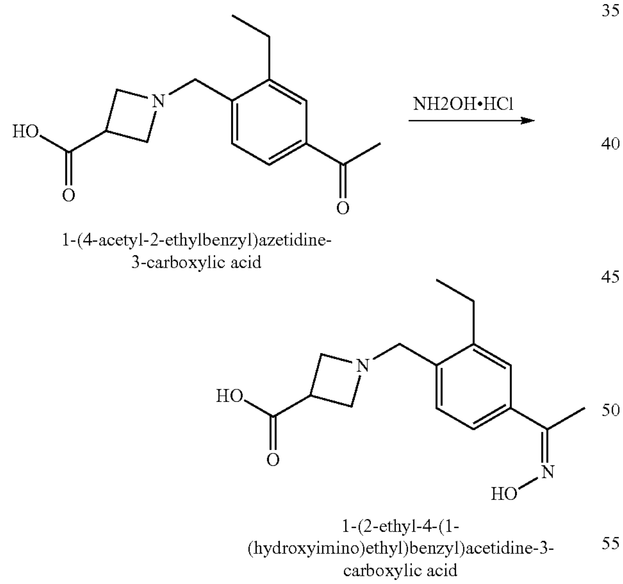

1-(4-acetyl-2-ethylbenzyl)azetidine-3-carboxylic acid 1-(2-ethyl-4-(1-(hydroxyimino)ethyl)benzyl)acetidine-3-carboxylic acid To a stirred solution of 1-(4-acetyl-2-ethylbenzyl)azetidine-3-carboxylic acid (Compound IV) (10 g) in methanol-water (100 ml) was added hydroxylamine hydrochloride (10 g) in 50% sodium hydroxide solution. The reaction mixture was heated to 60° C. for 10 hours and then cooled to room temperature. The reaction mixture neutralized with acetic acid to yield 1-(2-ethyl-4-(1-(hydroxyimino)ethyl)benzyl) azetidine-3-carboxylic acid (Compound III) as oil.

Example D: Synthesis of Siponimod (I)

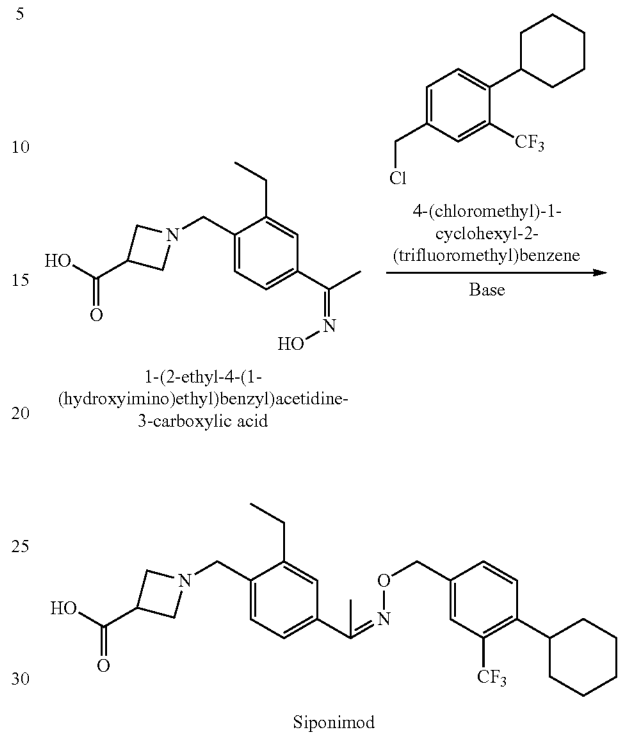

1-(2-ethyl-4-(1-(hydroxyimino)ethyl)benzyl)acetidine-3-carboxylic acid

Siponimod

To a stirred solution of 1-(2-ethyl-4-(1-(hydroxyimino) ethyl)benzyl)azetidine-3-carboxylic acid (Compound III) (10 g) and 4-(chloromethyl)-1-cyclohexyl-2-(trifluoromethyl) benzene (Compound II) (10 g) in methylene chloride (100 ml) was added the triethyl amine (10 ml). The reaction mixture was stirred at room temperature for 10 hours. The reaction mixture was washed with water. The organic layer was washed with brine solution and dried over anhydrous sodium sulfate. The organic layer was concentrated under reduced pressure at 40° C. to yield Siponimod. The crude product is further purified by silica gel column chromatography to yield 18 g of pure Siponimod (I).

Example 2: Synthesis of Siponimod

Example A: Synthesis of 4-acetyl-2-ethylbenzyl methanesulfonate (Compound XIII) (R2-mesyl)

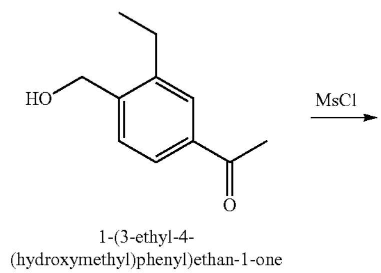

1-(3-ethyl-4-(hydroxymethyl)phenyl)ethan-1-one

-continued

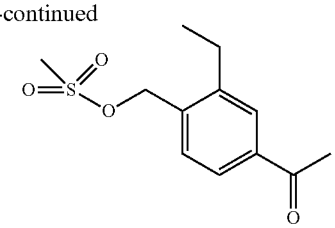

4-acetyl-2-ethylbenzyl methanesulfonate 1-(3-ethyl-4-(hydroxymethyl)phenyl)ethan-1-one (Compound VII) (50 g) was dissolved in toluene (500 ml) and cooled to 0-5° C. Charged methane sulfonyl chloride (50 ml) at 0-5° C. The temperature of the reaction mass was raised to 50-55° C. and stirred for 4 hours at same temperature. The reaction mass was cooled to room temperature and washed with water. The organic layer was separated and solvent was removed completely under vacuum at 45-50° C. to yield 60 g of 4-acetyl-2-ethylbenzyl methanesulfonate (compound XIII) as an oily residue. Purity (98.5%).

The oily residue was used in the next step without further purification.

Example B: Synthesis of methyl 1-(4-acetyl-2-ethylbenzyl)azetidine-3-carboxylate (Compound XI) (R1 is methyl)

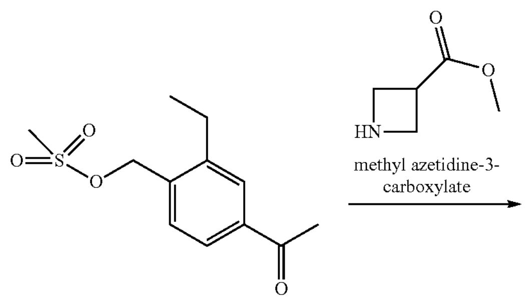

4-acetyl-2-ethylbenzyl methanesulfonate

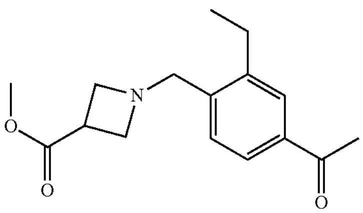

methyl 1-(4-acetyl-2-ethylbenzyl)azetidine-3-carboxylate 4-acetyl-2-ethylbenzyl methanesulfonate (compound XIII) (30 g) and methylazetidine-3-carboxylate (compound XII) (R1 is methyl) (27.2 g) dissolved in methanol (100 ml). Added triethylamine (31 ml) at 0-5° C. The temperature of the reaction mass was raised to 25-30° C. and stirred for 24 hours at same temperature. Methanol was removed completely under vacuum. The water (300 ml) and ethyl acetate (150 ml) were added to the reaction mass and stirred further for 30 min. The organic layer was separated and solvent was removed completely under vacuum to yield 32 g of methyl 1-(4-acetyl-2-ethylbenzyl)azetidine-3-carboxylate (compound XI) as brown oily residue. Purity 95.6%.

The oily residue was used in the next step without further purification

Example C: Synthesis of methyl ester of Siponimod (Compound X) (R1 is methyl)

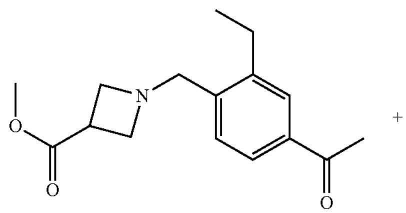

methyl 1-(4-acetyl-2-ethylbenzyl)azetidine-3-carboxylate

+

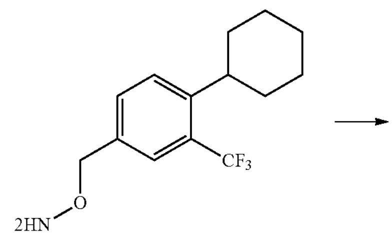

O-(4-cyclohexyl-3-(trifluoromethyl)benzyl)hydroxylamine

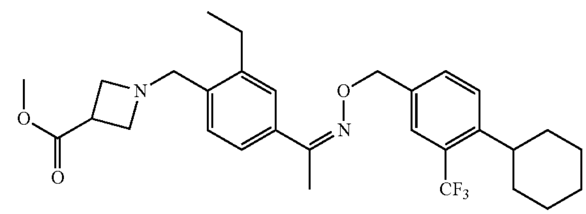

Methyl ester of Siponimod methyl 1-(4-acetyl-2-ethylbenzyl)azetidine-3-carboxylate (Compound XI) (10 g) and O-(4-cyclohexyl-3-(trifluoromethyl)benzyl)hydroxylamine (Compound IX) (15 g) were dissolved in IPA (100 ml). The temperature of the reaction mass as raised to 50-55° C. and maintained at same temperature for 1 hour. The solvent was removed completely under vacuum to yield 13.2 g of methyl ester of Siponimod (compound X) as a yellow thick oily mass.

Purity 96.4%

Example D: Synthesis of Compound of Formula-I (Siponimod)

methyl ester of Siponimod (Compound X) (10 g) was dissolved in methanol (100 ml). A IN solution of sodium hydroxide (100 ml) was added and the reaction mass was stirred for 3 hours at room temperature. Ethyl acetate (100 ml) was added and the pH of reaction mass was adjusted to 6.0-6.5 with acetic acid. The organic layer was separated, washed with water. The solvent was removed completely under vacuum. The residue was stirred in a mixture of methyl tertiary butyl ether and heptane to yield 6 g of title compound. Purity 98.5%

Example 3: Synthesis of Siponimod (I)

Example A: Synthesis of 1-(4-(chloromethyl)-3-ethylphenyl) ethan-1-one (Compound VI)

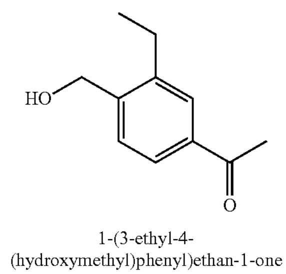

1-(3-ethyl-4-(hydroxymethyl)phenyl)ethan-1-one chlorination

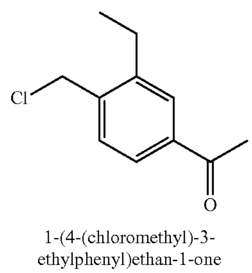

1-(4-(chloromethyl)-3-ethylphenyl)ethan-1-one

To a stirred solution of 1-(3-ethyl-4-(hydroxymethyl) phenyl)ethan-1-one (Compound VII) (100 g) in toluene (1000 ml) was added TEA (150 ml) at 0-10° C. Charged methane sulfonyl chloride (100 ml) slowly maintaining temperature at 0-10° C. The temperature of the reaction mass was raised to 50-55° C. and stirred for 4.0 hours at same temperature. Charged water (1000 ml) at 25-30° C. and stirred for 15-20 minutes. The organic layer was separated and washed with water (4×1000 ml). The organic layer was washed with brine solution (1000 ml) and dried over anhydrous sodium sulfate. The solvent was removed completely under vacuum at 50-55° C. to yield 110 g of 1-(4-(chloromethyl)-3-ethylphenyl) ethan-1-one (Compound VI) as yellow oil.

The oily residue was used in the next step without further purification.

Example B: Synthesis of methyl 1-(4-acetyl-2-ethylbenzyl)azetidine-3-carboxylate (Compound XI) (R1 is methyl)

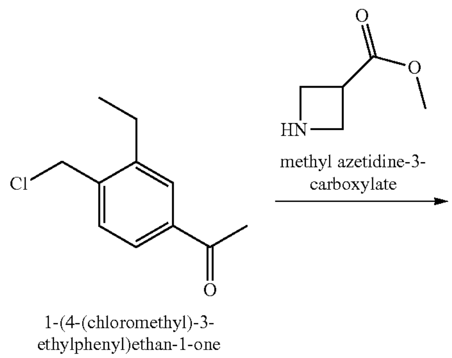

1-(4-(chloromethyl)-3-ethylphenyl)ethan-1-one

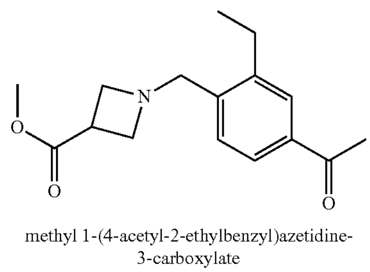

methyl 1-(4-acetyl-2-ethylbenzyl)azetidine-3-carboxylate 1-(4-(chloromethyl)-3-ethylphenyl) ethan-1-one (Compound VI) (100 g) oil dissolved in DMF (500 ml) at 25-30° C. Added triethylamine (150.0 ml) at 25-30° C. Added methyl azetidine-3-carboxylate (Compound XII) (120 g) in lots to the reaction mass. The temperature of the reaction mass was raised to 45-50° C. and stirred for 2 hours at same temperature. Water (1800 ml) and ethyl acetate (1000 ml) were added to the reaction mass and stirred further for 30 min. The organic layer was separated, water (1000 ml) was added and pH of the reaction mass was adjusted to 1-2 with dil. HCl. The aqueous layer was separated, pH of the reaction mass was adjusted to 6-7 with DIPEA. Extracted with ethyl acetate (1000 ml). The organic layer was separated, washed with water (500 ml) and solvent was removed completely under vacuum at 45-50° C. to yield 120 g of methyl 1-(4-acetyl-2-ethylbenzyl)azetidine-3-carboxylate (compound XI) as brown oily residue.

The oily residue was used in the next step without further purification.

Example C: Synthesis of fumarate Salt of methyl ester of Siponimod (Compound X) (R1 is methyl)

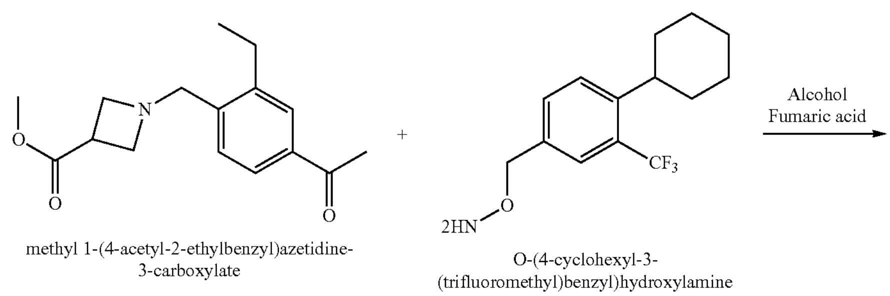

methyl 1-(4-acetyl-2-ethylbenzyl)azetidine-3-carboxylate

O-(4-cyclohexyl-3-(trifluoromethyl)benzyl)hydroxylamine

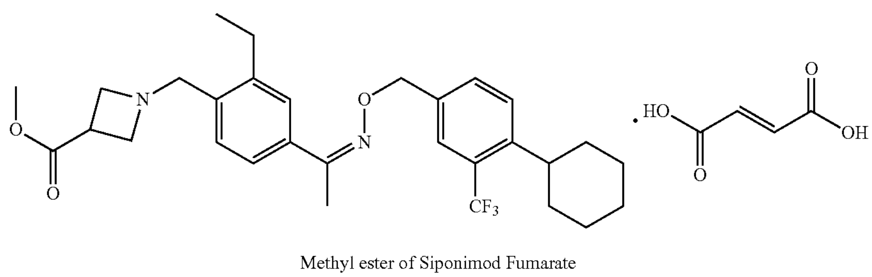

Methyl ester of Siponimod Fumarate methyl 1-(4-acetyl-2-ethylbenzyl)azetidine-3-carboxylate (Compound XI) (100 g) was dissolved in methanol (500 ml). The pH of the rection mass was adjusted to 0 to 1 with dilute HCl. Charged O-(4-cyclohexyl-3-(trifluoromethyl)benzyl) hydroxylamine (Compound IX) (120 g). The reaction mass was stirred at 25-30° C. for 5-6 hours. Water (1000 ml) and ethyl acetate (1000 ml) were added to the reaction mass and stirred further for 30 min. The pH of the reaction mass was adjusted to 7-8 with DIPEA. The organic layer was separated, washed with water (500 ml) and solvent was removed completely under vacuum at 45-50° C. to yield residue. The residue was dissolved in IPA (600 ml) and treated with fumaric acid (40 g). The temperature of the reaction mass was raised to 70-75° C. and stirred for 30 minutes at same temperature. The reaction mass was cooled to 25-30° C. and stirred for 60 minutes. The solids were isolated by filtration, washed with IPA and dried under vacuum at 50° C. to yield 160 g of fumarate salt of methyl ester of Siponimod (compound X).

Example D: Synthesis of Compound of Formula-I (Siponimod)

Fumarate salt of methyl ester of Siponimod (Compound X) (100 g) was stirred in a mixture of water (1000 ml) and ethyl acetate (1000 ml). The pH of reaction mass was adjusted to 6-7 with TEA and stirred at 25-30° C. for 15-20 minutes. The organic layer was separated washed with 5% NH4Cl solution. The solvent was removed completely under vacuum at 45-50° C. Added 4% NaOH solution (1000 ml) at 25-30° C., followed by IPA (1000 ml) and stirred the reaction mass at 25-30° C. for 1 hour. The pH of reaction mass was adjusted to 4.5-5 with acetic acid. Water (4000 ml) was added, and the reaction mass was stirred at 25-30° C. for 20 hours. The solids were isolated by filtration, washed with water and dried under vacuum at 45-50° C. for 10 hours to yield 70 g of Siponimod (compound I).

Example 4: Purification of Siponimod (I)

Siponimod (70 g) was stirred in acetone (350 ml) at 40-45° C. for 30 minutes. The reaction mass was cooled to 25-30° C., further chilled to 0-5° C. and stirred for 60 minutes. The solids were isolated by filtration, washed with chilled acetone and dried under vacuum at 45-50° C. for 10 hours to yield 60-65 g of Siponimod (compound I).

Example 5: Synthesis of oxalate salt of O-(4-cyclohexyl-3-(trifluoromethyl)benzyl)hydroxylamine (Compound IX)

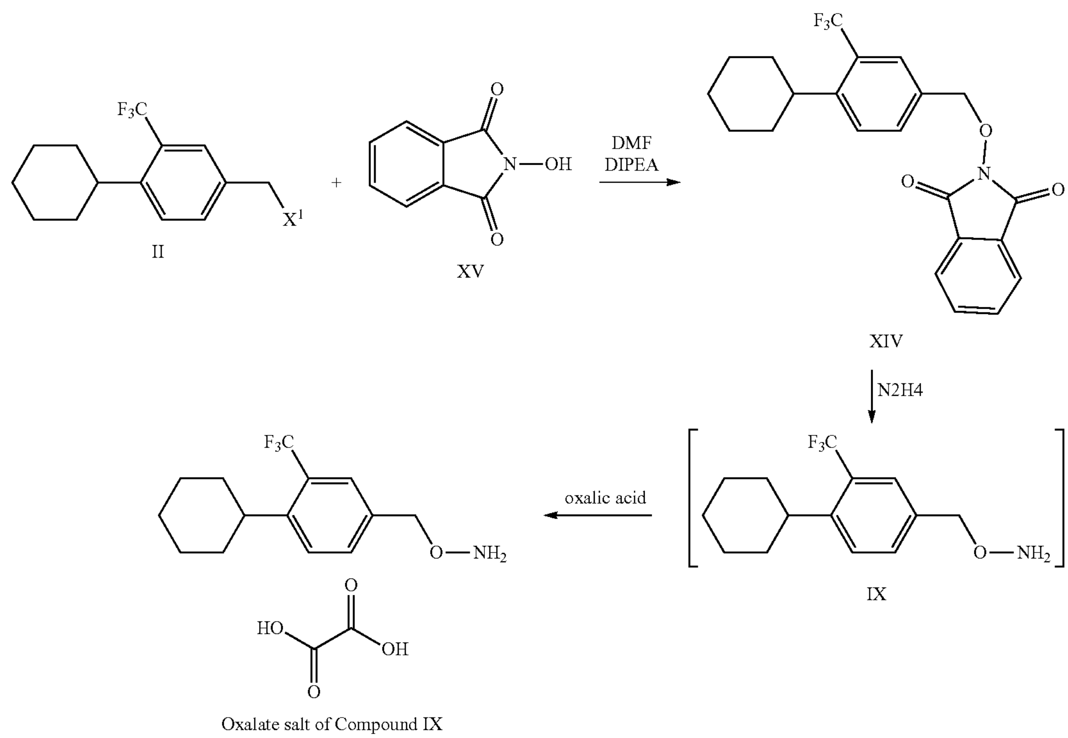

II

XV

XIV

IX

Oxalate salt of Compound IX

To a stirred solution of 4-(chloromethyl)-1-cyclohexyl-2-(trifluoromethyl) benzene (Compound II) in DMF (10 vol) was added n-hydroxy phthalimide (compound XV) (1.5 moles eq) at 25-30° C. Charged diisopropylethylamine (0.1 mol eq). The temperature of the reaction mass was raised to 65-70° C. and stirred for 1 hour. The rection mass was cooled to 25-30° C. and stirred for another 1 hour. The solids were isolated by filtration, washed with water and dried under vacuum to yield 24(4-cyclohexyl-3-trifluoromethyl) benzyl)oxy)isoindoline-1,3-dione (compound XIV).

Compound XIV was dissolved in THF (10 vol). Charged Hydrazine hydrochloride (1.8 mol eq). The reaction mass was stirred for 3-4 hours at 25-30° C. After completion of reaction, the insoluble were removed by filtration. The clear filtrate was concentrated under reduced pressure at 40° C. The residue was dissolved in a mixture of water (10 vol) and ethyl acetate (10 vol). The organic layer was separated, washed with water and dried over anhydrous sodium sulfate. Oxalic acid (0.2 mol eq) was added to the organic layer and stirred for 3-4 hours at 25-30° C. The solids were isolated by filtration, washed and dried under reduced pressure at 40° C. to yield oxalate salt of O-(4-cyclohexyl-3-(trifluoromethyl) benzyl)hydroxylamine (Compound IX).

Example 6: Synthesis of Siponimod Fumarate Form-C1

Siponimod fumarate amorphous (3 g) was suspended in (20 V) n-Heptane and stirred for 20-22 hours at Room temperature. The material was filtered under vacuum and dried in the VTD at 45-50° C. for 3-4 hours to obtain the title compound.

Water content: 3.63%.

Residual solvents: Heptane: 84 ppm.

The sample was subsequently analysed and showed the spectrum of Crystalline Form-C1, which is depicted as XRPD in FIG. 1, DSC in FIG. 2 and TGA in FIG. 3.

Example 7: Synthesis of Siponimod Fumarate Form-C2

Siponimod fumarate amorphous (2 g) was dissolved in (2 V) NMP. To the above clear solution charged (8 V) of water and stirred for 2-3 hours at Room temperature. The material was filtered under vacuum and washed with (3 V) of water and dried in the VTD at 55-60° C. for 3-5 hours to obtain the title compound.

Water content: 1.79%

Residual solvents: NMP content: 40,775 ppm, Methanol: 48 ppm.

The sample was subsequently analysed and showed the spectrum of Crystalline Form-C2, which is depicted as XRPD in FIG. 4, DSC in FIG. 5 and TGA in FIG. 6.

Example 8: Synthesis of Siponimod Adipic Acid Co-Crystal Form-C1

Siponimod (2 g) and adipic acid (0.28 g) (2:1 mole/mole) was dissolved in (25 V) of ethanol at 55-60° C. Then distilled under vacuum at 55-60° C. To the crude charged (30 V) of acetonitrile and stirred for 17-19 hours at room temperature (~25° C.). The material was filtered under vacuum and dried in the VTD at 45-50° C. for 3-4 hours to obtain the title compound. Water content: 0.89%, Adipic acid content: 12.46%

Residual solvents: Ethanol −40 ppm; Acetonitrile-11 ppm; IPA—ND; N-heptane—ND

ND—Not detected

The sample was subsequently analysed and showed the spectrum of Crystalline Form-C1, which is depicted as XRPD in FIG. 12, DSC in FIG. 13, TGA in FIG. 14, Solid state $^{13}C$ NMR in FIG. 15, Raman spectra in FIG. 16 and an ORTEP diagram in FIG. 17.

Example 9: Synthesis of Siponimod Glutaric Acid Co-Crystal Form-C1

Siponimod (0.25 g) and glutaric acid (0.032 g) (2:1 mole/mole) was dissolved in (28 V) of ethanol at 55-60° C. Then distilled under vacuum at 55-60° C. To the crude charged (24 V) acetonitrile and (24 V) diisopropyl ether stirred for 15-18 hours at room temperature. The material was filtered under vacuum and dried in the VTD at 45-50° C. for 3-4 hours to obtain the title compound.

The sample was subsequently analysed and showed the spectrum of Crystalline Form-C1, which is depicted as XRPD in FIG. 18, DSC in FIG. 19 and TGA in FIG. 20.

Example 10: Synthesis of Siponimod Base

Figure 21:
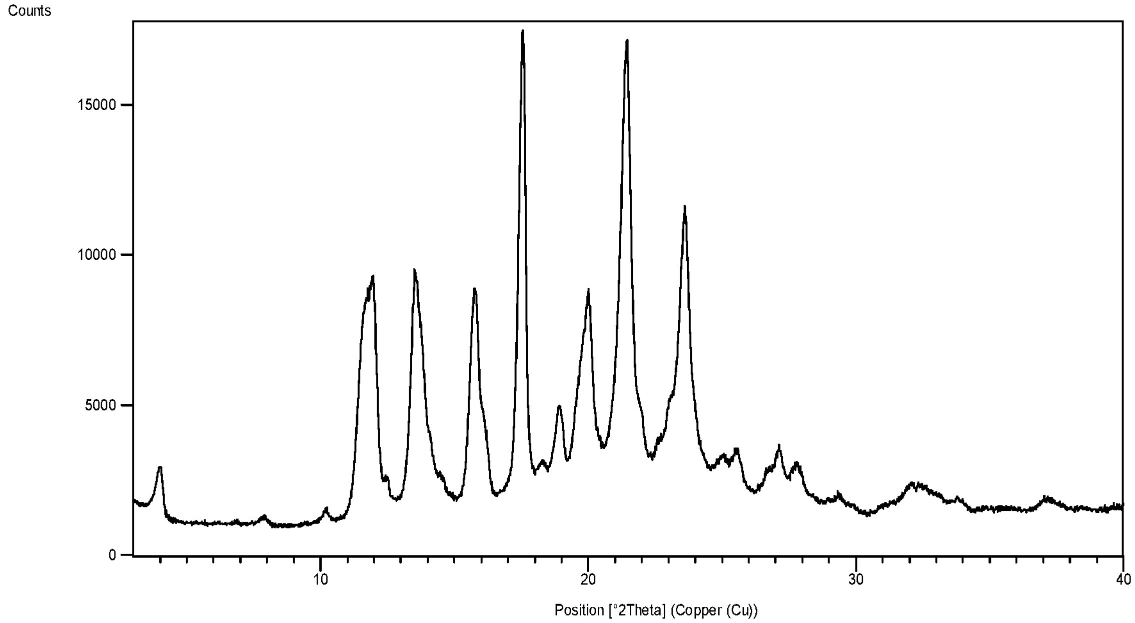
FIG. 21 depicts X-Ray Powder Diffraction (XRPD) pattern of Siponimod base Form-C1

Siponimod fumarate (2 g) was suspended in (20 V) ethyl acetate and (10 V) water. To the above suspension slowly charged (0.5 V) of tri ethyl amine and stirred for 1 hour at 20-25° C. Separated layers and collected ethyl acetate layer and back extracted aqueous layer with (20 V) of ethyl acetate. Washed Ethyl acetate layer with 10% sodium dihydrogen orthophosphate solution (20 V). Then collected ethyl acetate layer and dried on sodium sulphate. Then distilled ethyl acetate layer under vacuum at 45-50° C. Stripped oily mass with (10 V) of isopropyl acetate and distilled under vacuum at 45-50° C. To the above crude charged (5 V) of iso propyl acetate and (15 V) of n-Heptane and stirred for 14-16 hours at room temperature. Then filtered the material under vacuum and dried the material in VTD at 45-50° C. for 4-6 hours to obtain the title compound The sample was subsequently analysed by XRPD and showed the spectrum of Crystalline Form-C1, which is shown in FIG. 21.

Example 11: Preparation of Siponimod Fumarate Form-C3

Siponimod fumarate amorphous (3 g) was dissolved in isopropyl alcohol (4V) at 50-55° C. In another RBF was taken n-heptane (20V) and chilled to below −15° C. The chilled solution of n-Heptane was seeded with Siponimod fumarate Form-C3 seed and maintained the RBF temperature at −15° C. to −10° C. To the obtained seed slurry, clear solution of Siponimod fumarate was added slowly and reaction mass was stirred at same temperature for 0.5-1 hour. The stirring continued further at 0-5° C. for 0.5-1 hour. The material was filtered under vacuum and dried in VTD at 40-45° C. for 3-4 hours to obtain 2.7 gm of the title compound.

Water content: 0.58%

Residual solvents: IPA-ND, Heptane-373 ppm, Methanol-11 ppm.

The sample was subsequently analysed and showed the spectrum of Crystalline Form-C3, which is depicted as XRPD in FIG. 7, DSC in FIG. 8, TGA in FIG. 9, Solid state $^{13}C$ NMR in FIG. 10 and Raman spectra in FIG. 11.

Example 12: Preparation of Siponimod Fumarate Form-C3

Dissolved Siponimod crude (60 g) in Isopropyl alcohol (360 ml) at 45-50° C. and then cooled to RT. In another flask was prepared a solution of Fumaric acid (6.73 g) in Isopropyl alcohol (190 ml) at 60-65° C. and cooled to RT. In another flask, was charged n-Heptane (1400 ml) and cooled to 0-5° C. To the pre-chilled n-heptane, was added Siponimod fumarate Form C3 seed (6.5 g) and stirred to get suspension. To the resulted suspension was added simultaneously, above Siponimod solution and Fumaric acid solution, over a period of 15-30 min at 0-5° C. The reaction mass was stirred for 2-3 hours at 0-5° C. The solids were isolated by filtration, washed with n-Heptane (50 ml), and dried at 40-45° C. in VTD for 4-6 hours to obtain 65 gm of the title compound.

The sample was subsequently analysed and showed the spectrum of Crystalline Form-C3, which is depicted as XRPD in FIG. 7, DSC in FIG. 8, TGA in FIG. 9, Solid state $^{13}C$ NMR in FIG. 10 and Raman spectra in FIG. 11.

We claim:

1. A Siponimod adipic acid co-crystal, or a solvate or hydrate, and premixes thereof.

2. The Siponimod adipic acid co-crystal according to claim 1, wherein the mole ratio of Siponimod to adipic acid is ranging from 1:0.25 to 1:1.2.

3. The Siponimod adipic acid co-crystal according to claim 1, wherein the co-crystal has an XRD pattern comprising peaks at 6.50, 16.79, and 21.85±0.2° 2θ.

4. The Siponimod adipic acid co-crystal according to claim 1 in a crystalline Form.

5. A process for preparing Siponimod adipic acid co-crystal according to claim 1, the process comprising:

a) dissolving Siponimod and adipic acid in a first organic solvent at a temperature of 25° C. to a reflux temperature of the first organic solvent;

b) removing the first organic solvent to produce a residue;

c) stirring the residue in a second organic solvent for at least 1 hour to 30 hours at 25-30° C. to produce a precipitate of the Siponimod adipic acid co-crystal;

d) isolating the precipitate of the Siponimod adipic acid co-crystal; and e) drying the isolated precipitate at 30-60° C. for at least 1 hour to 10 hours.

6. The process according to claim 5, wherein the Siponimod is in a polymorphic form or in a mixture of polymorphic forms.

7. The process according to claim 5, wherein the first organic solvent is selected from the group comprising of C1 to C5 alcohols; nitriles; C1 to C6 halogenated hydrocarbons; C6 to C14 aromatic hydrocarbons, C2 to C7 esters; C4 to C7 ethers; cyclic ether; aromatic ethers; DMF, DMSO, and mixtures thereof.

8. The process according to claim 5, wherein the first organic solvent is selected from the group comprising of methanol, ethanol, isopropanol, t-butanol, acetonitrile, propionitrile, dichloromethane, dichloroethane, chloroform, carbon tetrachloride, toluene, xylene, ethylbenzene, propylbenzene, butylbenzene, trimethylbenzene, tetramethylbenzene, cyclohexylbenzene, ethyl acetate, methyl acetate, isopropyl acetate, dimethyl ether, diethyl ether, ethyl methyl ether, tetrahydrofuran, 1,4-dioxane, diphenyl ether, DMF, DMSO, and mixtures thereof.

9. The process according to claim 5, further comprising: prior to step (a), preparing the siponimod by converting a compound of Formula XI:

XI

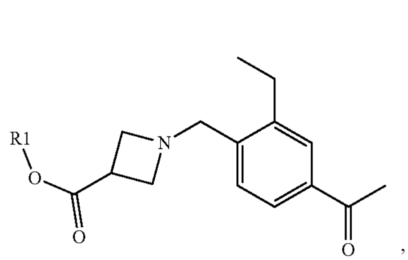

wherein R1 is a C1-C4 alkyl group, to siponimod.

10. The process according to claim 9, wherein converting the compound of Formula XI comprises:

reacting the compound of Formula XI with a compound of Formula IX or a salt thereof:

IX

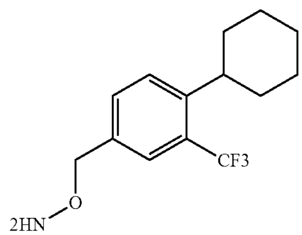

in the presence of a solvent to provide a compound of Formula X or a salt thereof:

X

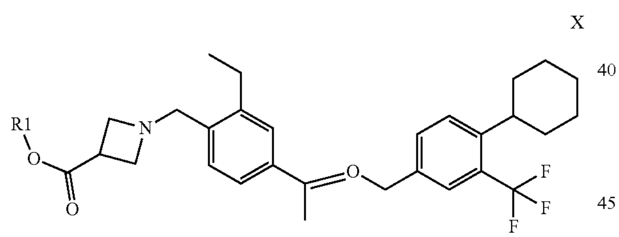

wherein R1 is the C1-C4 alkyl group; and hydrolyzing the compound of Formula X or the salt thereof in the presence of an acid or a base to provide the Siponimod.

11. The process according to claim 9, further comprising preparing the compound of Formula XI by i) reacting a compound of Formula XIII:

XIII

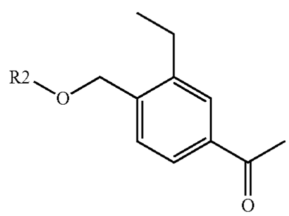

wherein R2 is a leaving group selected from the group consisting of alkyl sulfonyl, aryl sulfonyl, and acetyl, with a compound of Formula XII:

XII

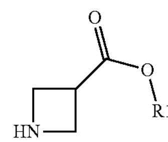

wherein R1 is the C1-C4 alkyl group, in the presence of a first base and a first solvent to provide the compound of Formula XI; or ii) reacting a compound of Formula VI:

VI

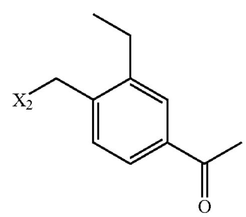

wherein $X_2$ is a leaving group selected from the group consisting of chloro, bromo, and iodo, with the compound of Formula XII in the presence of a second base and a second solvent, to provide the compound of Formula XI.

12. The process according to claim 10, wherein the compound of Formula IX or the salt thereof is prepared by reacting a compound of Formula II:

II

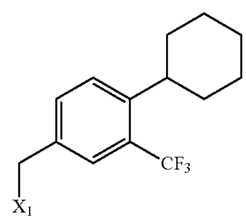

wherein $X_1$ is a leaving group selected from the group consisting of bromo, chloro, iodo, and fluoro, with n-hydroxy phthalimide of Formula XV

XV

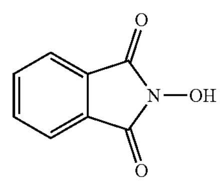

in the presence of a second base and a second solvent to provide a compound of Formula XIV

XIV

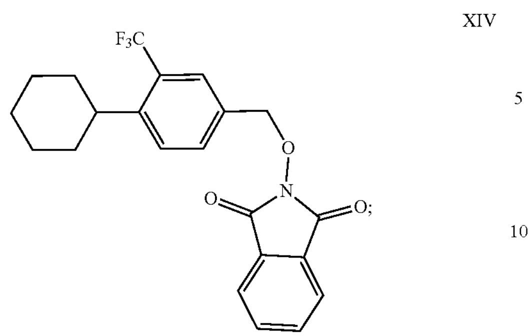

reacting the compound of Formula XIV with hydrazine or a salt thereof in the presence of a third solvent to provide the compound of Formula IX; and optionally converting the compound of Formula IX to the salt thereof.

13. A pharmaceutical composition, comprising the Siponimod adipic acid co-crystal according to claim 1, and one or more pharmaceutically acceptable excipients.

14. A method of treating a relapsing form of multiple sclerosis in a patient in need of such treatment, comprising administering to the patient a therapeutically effective amount of the Siponimod adipic acid co-crystal according to claim 1.

* * * * *